US009376477B2

(12) United States Patent
Grabulovski et al.

(10) Patent No.: US 9,376,477 B2
(45) Date of Patent: Jun. 28, 2016

(54) IL-17 BINDING COMPOUNDS AND MEDICAL USES THEREOF

(75) Inventors: Dragan Grabulovski, Zurich (CH); Michela Silacci Melkko, Zurich (CH); Frédéric Mourlane, Olten (CH); Simon Sebastian Brack, Winterthur (CH); Julian Bertschinger, Hombrechtikon (CH); Nadja Baenziger, Schlieren (CH); Sarah Batey, Zurich (CH)

(73) Assignee: Covagen AG, Zug (CH)

(*) Notice: Subject to any disclaimer, the term of this patent is extended or adjusted under 35 U.S.C. 154(b) by 24 days.

(21) Appl. No.: 13/392,783

(22) PCT Filed: Aug. 24, 2010

(86) PCT No.: PCT/EP2010/062314
§ 371 (c)(1),
(2), (4) Date: Sep. 14, 2012

(87) PCT Pub. No.: WO2011/023685
PCT Pub. Date: Mar. 3, 2011

(65) Prior Publication Data
US 2013/0005659 A1    Jan. 3, 2013

(30) Foreign Application Priority Data
Aug. 27, 2009   (EP) .................................... 09010950

(51) Int. Cl.
A61K 38/00    (2006.01)
C07K 14/47    (2006.01)

(52) U.S. Cl.
CPC ......... *C07K 14/4703* (2013.01); *C07K 2319/00* (2013.01); *C07K 2319/30* (2013.01); *C07K 2319/31* (2013.01); *C07K 2319/55* (2013.01); *C07K 2319/70* (2013.01)

(58) Field of Classification Search
None
See application file for complete search history.

(56) References Cited

U.S. PATENT DOCUMENTS 7,029,912 B1 *   4/2006   Phan et al. .................... 435/325
7,072,771 B2 *   7/2006   Oliveira ......................... 702/27

FOREIGN PATENT DOCUMENTS

| CN | 101506230 | 8/2009 |
| EP | 1 541 694 | 6/2005 |
| WO | 2005/051422 | 6/2005 |
| WO | 2006/054059 | 5/2006 |
| WO | 2007/038703 | 4/2007 |
| WO | WO 2008/022759 | 2/2008 |

OTHER PUBLICATIONS

Weng et al. Structure-Function Analysis of SH3 Domains: SH3 Binding Specificity Altered by Single Amino Acid Substitutions. Mol Cell Biol. Oct. 1995; 15(10):5627-34.*
Bertschinger, J. Covagen Advanced Biopharmaceuticals, May 2011.*
Accession No. AK171646 "*Mus musculus* Fyn proto-oncogen" (Sep. 19, 2008).
Grabulovski, et al. (2007) "A novel, non-immunogenic Fyn SH3-derived binding protein with tumor vascular targeting properties." *The Journal of Biological Chemistry* 282(5): 3196-3204.
Ivanov, et al. (2009) "Interleukin-17 as a drug target in human disease." *Trends in Pharmacological Sciences* 30(2): 95-103.
Lee, et al. (1995) *The EMBO Journal* 4(20): 5006-5015.
Viti, et al. (2000) *Methods Enzymol.* 326: 480-505.
Baeten et al. (2014) American College of Rheumatology Meeting Abstracts [Abstract No. 819].
Brack et al. (2014) *Mol Cancer Ther.* 13(8): 2030-2039.
Chung et al. (2013) *Nature Medicine* 9(19): 1114-1123.
De Bruyn et al. (2012) *Arthritis Rheum* vol. 62, Nov. 2012 Abstract Supplement.
Grabulovski et al. (2013) *Arthritis Rheum* vol. 65, Oct. 2013 Abstract Supplement.
Holt et al. (2008) *Protein Engineering, Design & Selection* 21: 283-288.
Hueber et al. (2010) *Sci Transl Med* 2(52): 52-72.
Leonardi et al. (2012) *N. Engl. J. Med.* 266: 1190-1199.
Löfblom et al. (2010) *FEBS Letters* 584(12): 2670-2680.
Marry, Human Biochemistry Moscow MIR 1993 vol. 1, p. 34.
McInnes et al. (2014) American College of Rheumatology Meeting Abstracts [Abstract No. L1].
Miossec et al. (2009) *N England Med* 361: 888-898.
Mross et al. (2013) *PLoS One* 8(12): e83232.
Nygren & Skerra (2004) *Journal of Immunological Methods* 290: 3-28.
Silverman et al. (2005) *Nature Biotechnology* 23: 6 pages.
Steffen et al. (2006) *European Journal of Nuclear Medicine and Molecular Imaging* 33: 631-638.
Tolcher et al. (2011) *Clinical Cancer Research* 17: 363-371.
van den Berg & McInnes (2013) *Semin Arthritis Rheum.* 43(2): 158-170.
Walker et al. (2010) *Protein Engineering, Design & Selection* 23: 271-278.
Chabaud, et al. *Cytokine* (2000) 12(7): 1092-1099.
Layh-Schmitt & Colbert *Curr Opin Rheumatol.* (2008) 20(4): 392-397.
Miossec *Eur. J. Immunol.* (2009) 39: 634-675.
Miossec *Microbes and Infection* (2009) 625-630.
Sato, et al. *The Journal of Experimental Medicine* (2006) 203(12): 2673-2682.
Bulina et al. (2006) *Nature Biotechnology* 24(1): 95-99.

* cited by examiner

*Primary Examiner* — Dong Jiang

(74) *Attorney, Agent, or Firm* — Hunton & Williams LLP

(57) ABSTRACT

The present invention relates to new IL-17 inhibiting polypeptides, corresponding fusion proteins, compositions and medical uses thereof.

15 Claims, 10 Drawing Sheets

IL-17 BINDING COMPOUNDS AND MEDICAL USES THEREOF

CROSS-REFERENCE TO RELATED APPLICATIONS

This application is the U.S. National Stage filing of International Application No. PCT/EP2010/062314, filed Aug. 24, 2010, which claims priority to EP 09010950.5, filed Aug. 27, 2009, the disclosure of which is hereby incorporated by reference.

The present invention relates to new IL-17 inhibiting polypeptides, corresponding fusion proteins, compositions and medical uses thereof.

BACKGROUND OF THE INVENTION

CD4+ T cells play a central role in orchestrating immune responses by assisting other cells of the adaptive or innate immune system. In early studies two classes of CD4+ T cells (Th1 and Th2) were identified. More recently, a new subset of CD4+ T cells, the Th17 lineage was identified. Th17 cells appear to have evolved as a branch of the adaptive immune system specialized in enhanced host protection against extracellular bacteria as well as some fungi and microbes not well covered by Th1 or Th2 immunity.

Th17 cells were identified in the context of the discovery of a new cytokine family, the IL-17 family, which is presently known to comprise six members (IL-17A-F). IL-17 (previously named CTLA-8) is mainly expressed by Th17 cells and was designated IL-17A to indicate that it is the founding member of this cytokine family. IL-17 members share no sequence homology with other presently known mammalian proteins and therefore constitute a distinct cytokine family. Structural features of IL-17 family members deduced from the crystal structure of IL-17F suggest that, similar to many cytokines, each of the family members is probably produced as a homodimer, although structural similarities imply that heterodimers may exist. Very recently, a heterodimer of IL-17A and IL-17F expressed by activated human CD4+ T cells was identified that signals through the IL-17RA/IL-17RC complex (Wright J. F. et al. (2008) J. of Immunol., 181, p. 2799-2805).

The identification of Th17 cells as central mediators in chronic inflammatory processes and as principal pathogenic effectors in several types of autoimmunity conditions previously thought to be Th1-mediated promises new therapeutic approaches (Weaver T. et al. (2008) Annu. Rev. Immunol., 25, p. 821-852). Indeed, the proinflammatory cytokine IL-17 is mainly expressed by Th17 cells and is present at elevated levels in synovial fluid of patients with rheumatoid arthritis (RA) and has been shown to be involved in early RA development. In addition, IL-17 is a potent inducer of TNF-alpha and IL-1, the latter being mainly responsible for bone erosion and the very painful consequences for affected patients (Lubberts E. (2008) Cytokine, 41, p. 84-91). Furthermore, inappropriate or excessive production of IL-17 is associated with the pathology of various other diseases and disorders, such as osteoarthritis, loosening of bone implants, acute transplant rejection (Antonysamy et al., (1999) J. Immunol, 162, p. 577-584; van Kooten et al. (1998) J. Am. Soc. Nephrol., 9, p. 1526-1534), septicemia, septic or endotoxic shock, allergies, asthma (Molet et al. (2001) J. Allergy Clin. Immunol., 108, p. 430-438), bone loss, psoriasis (Teunissen et al. (1998) J. Invest. Dermatol, 111, p. 645-649), ischemia, systemic sclerosis (Kurasawa et al. (2000) Arthritis Rheum., 43, p. 2455-2463), stroke, and other inflammatory disorders.

Consequently, anti-IL-17 compounds have potential as anti-inflammatory agents, a therapeutic approach in line with a number of in vivo studies demonstrating that IL-17 neutralization reduces inflammatory processes such as arthritis. For example, the early neutralization of endogenous IL-17 by an IL-17 receptor-IgG1-Fc fusion protein starting after the immunization protocol during the initial phase of arthritis suppresses the onset of experimental arthritis (Lubberts et al. (2001) J. Immunol., 167, p. 1004-1013). Moreover, treatment with a neutralizing anti-IL-17 antibody in an animal model after the onset of collagen-induced arthritis reduced joint inflammation, cartilage destruction and bone erosion (Lubberts et al. (2004) Arthritis and Rheumatism, 50; 650-659). Histological analysis confirmed the suppression of joint inflammation, and systemic IL-6 levels were significantly decreased after treatment with an anti-IL-17 antibody. In contrast, systemic as well as local IL-17 overexpression using an adenoviral vector expressing murine IL-17 accelerated the onset of collagen-induced arthritis (CIA) and aggravated synovial inflammation at the site (Lubberts et al. (2001) J. Immunol., 167, p. 1004-1013 and Lubberts et al. (2002), Inflamm. Res. 51, p102-104).

Even though antibodies are routinely employed for analytical, purification, diagnostic and therapeutic purposes due to their ease of production, high affinity and specificity to virtually any desired target antigen, these still have a number of serious drawbacks such as the necessity of complex mammalian cell production systems, a dependency on disulfide bond stability, the tendency of some antibody fragments to aggregate, limited solubility and last but not least, they may elicit undesired immune responses even when humanized. As a consequence, a recent focus for developing small globular proteins as scaffolds for the generation of novel classes of versatile binding proteins has emerged. For generating diversity and target specificity, typically surface components (e.g. extracellular loops) of a protein framework with suitable biophysical properties are combinatorially mutated for producing a protein library to be screened for the target binding specificities of interest (Binz, H. K., and Pluckthun, A. (2005) Curr. Opin. Biotechnol. 16, 459-469).

These non-immunoglobulin-derived binding reagents are collectively designated "scaffolds" (Skerra A. (2000) J. Mol. Recognit. 13, 167-187). More than 50 different protein scaffolds have been proposed over the past 10 to 15 years, the most advanced approaches in this field being (as summarized in Gebauer M and Skerra A. (2009) Curr Opinion in Chemical Biology 13:245-255): affibodies (based on the Z-domain of staphylococcal protein A), Kunitz type domains, adnectins (based on the 10th domain of human fibronectin), anticalins (derived from lipocalins), DARPins (derived from ankyrin repeat proteins), avimers (based on multimerized LDLR-A), affitins (based on Sac7d from the hyperthermophilic archaeon), and Fynomers, which are derived from the human Fyn SH3 domain.

In general, SH3 domains are present in a large variety of proteins participating in cellular signal transduction (Musacchio et al. (1994) *Prog. Biophys. Mol. Biol.* 61; 283-297). These domains do not occupy a fixed position within proteins and can be expressed and purified independently. More than 1000 occurrences of the domain are presently known with about 300 human SH3 domains (Musacchio A. (2003) *Advances in Protein Chemistry.* 61; 211-268). Although there is great sequence diversity among SH3 domains, they all share a conserved fold: a compact beta barrel formed by two anti-parallel beta-sheets (Musacchio A. (2003) *Advances in Protein Chemistry.* 61; 211-268). Typically, SH3 domains bind to proline-rich peptides containing a PXXP core-binding motif (Ren et al. (1993) *Science* 259; 1157-1161), but examples of unconventional SH3 binding sites have also been described (Karkkainen et al. (2006) *EMBO Rep.* 7; 186-191). Most of the SH3 domains sequenced so far have an overall length of approximately 60 to 65 amino acids, but some of them may feature as many as 85 amino acids due to inserts into the loops connecting the main conservative elements of the secondary structure (Koyama et al. (1993) *Cell* 72(6); 945-952). An alignment of different SH3 domains revealed conserved amino acid residues responsible for the proper structure formation as well as for the canonical proline-rich motif recognition (Larson et al. (2000) *Protein Science* 9; 2170-2180).

Recently the inventors demonstrated that the Fyn SH3 domain is a particularly attractive scaffold ("Fynomer") for the generation of binding proteins because it (i) can be expressed in bacteria in soluble form in high amounts, (ii) is monomeric and does not aggregate when stored in solution, (iii) is very stable ($T_m$ 70.5° C.), (iii) lacks cysteine residues, and (iv) is of human origin featuring an amino acid sequence completely conserved from mouse to man and, hence, non-immunogenic (Grabulovski et al. (2007) JBC, 282, p. 3196-3204).

The objective underlying the present invention is to provide new IL-17A binding molecules, in particular ones with high specificity and high affinity for IL-17A. It is a further objective to provide IL-17A-binding molecules, preferably IL-17 inhibitors, suitable for research, diagnostic and medical treatment, preferably for use in medicaments for treating and/or preventing IL-17A-mediated diseases and medical conditions.

Surprisingly, the above objectives were solved by polypeptides comprising an amino acid sequence selected from the group consisting of:

(i)

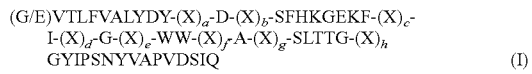

wherein a to h are 0 to 20,
preferably a is 1 to 10, more preferably 2 to 8, most preferably 6;
preferably b is 0 to 5, more preferably 1 to 3, most preferably 1;
preferably c is 0 to 5, more preferably 1 to 3, most preferably 1;
preferably d is 1 to 10, more preferably 3 to 9, most preferably 5 or 7;
preferably e is 0 to 5, more preferably 1 to 3, most preferably 1;
preferably f is 0 to 5, more preferably 1 to 3, most preferably 1;
preferably g is 0 to 5, more preferably 1 to 3, most preferably 1;
preferably h is 0 to 6, more preferably 1 to 3, most preferably 1 or 2;
(ii) an amino acid sequence having at least at least 70%, preferably at least 80%, more preferred at least 90%, most preferred at least 95% amino acid sequence identity to (i);
(iii) an amino acid sequence encoded by a nucleic acid that hybridizes to the complementary strand of a nucleic acid coding for (i), preferably under stringent conditions;
(iv) a fragment or functional derivative of (i) to (iii) derivable by substitution, addition and/or deletion of at least one amino acid,
wherein said polypeptide binds to IL-17A.

The above generic formula (I) is the result of the repetitive and extensive mutational analysis of the human Fyn SH3 scaffold and selection based on IL-17A binding.

The positions designated X can be varied widely for the type of amino acid(s) and also the number of amino acids. Preferably, none of X are cysteine. The preferred number of amino acids for X is indicated by subscripts a to h, all of which are preferably 0 to 20, more preferably 0 or 1 to 10.

In native human Fyn SH3 $(X)_a$ and $(X)_d$ would correlate with the RT- and the Src loop, respectively. It is preferred but not necessary that $(X)_a$ and $(X)_d$ provide a loop structure. Typical loop structures are known to encompass 2 to more than 20 amino acids (Larson et al. (2000) *Protein Science* 9; 2170-2180). Hence, it is preferred that $(X)_a$ and/or $(X)_d$ have 2 to 20 amino acids. Preferably, a is 1 to 10, more preferably 2 to 8, most preferably 6. Preferably d is 1 to 10, more preferably 3 to 9, most preferably 5 or 7. Preferably $(X)_a$ is TAFWPG, more preferably VAFWPG, most preferably KAFWPG. Preferably $(X)_d$ is LNSSE, more preferably TRTSD or LHTSD, most preferably LRTSD.

$(X)_b$, $(X)_c$, $(X)_e$, $(X)_f$ and $(X)_g$ are independently of one another preferably 0 to 5, more preferably 1 to 3, most preferably 1. $(X)_h$ is preferably 0 to 6, more preferably 1 to 3, most preferably 1.

In a most preferred embodiment formula (I) is:

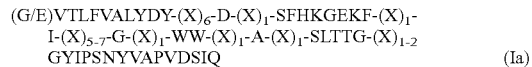

Of course, there are numerous variations in the amino acid sequence of formula (I) which will still allow for IL-17A binding of the polypeptides of the invention. Hence, the present invention also encompasses polypeptides comprising an amino acid sequence having at least 50, 60 or 70%, preferably at least 80%, more preferred at least 90%, most preferred at least 95% amino acid sequence identity to (i).

As used herein, the term "amino acid sequence identity" between amino acid sequences is meant to relate to the common and widely used alignment and comparison techniques of the person skilled in biochemistry. The amino acid sequence identity of two amino acid sequences can be determined by common alignment methods and tools. For example, for determining the extent of an amino acid sequence identity of an arbitrary polypeptide relative to the amino acid sequence of formula (I), the SIM Local similarity program can be employed (Xiaoquin Huang and Webb Miller, "A Time-Efficient, Linear-Space Local Similarity Algorithm." Advances in Applied Mathematics, vol. 12: 337-357, 1991.), that is freely available from the authors and their institute (see also the world wide web: http://www.expasy.org/tools/sim-prot.html); for multiple alignment analysis ClustalW can be used (Thompson et al., "CLUSTAL W: improving the sensitivity of progressive multiple sequence alignment through sequence weighting, position-specific gap penalties and weight matrix choice.", Nucleic Acids Res., 22(22): 4673-4680, 1994.). Preferably, the extent of the amino acid sequence identity of a polypeptide, a fragment or functional derivative of the invention to the amino acid sequence of formula (I) is determined relative to the complete sequence of formula (I).

Moreover, the present invention also encompasses polypeptides comprising an amino acid sequence encoded by a nucleic acid that hybridizes to the complementary strand of a nucleic acid coding for (i), preferably under stringent conditions. In other words, the amino acid sequence encompassed by polypeptides according to the invention is preferably defined indirectly by its coding nucleic acid that must still be capable of hybridizing to the complementary strand of a nucleic acid encoding the amino acid sequence of formula (I). Whether nucleic acids hybridize to one another is regularly determined in the art by specific alignment and comparison tools as well as experimentally. Next to common and/or standard protocols in the prior art for determining the ability of one nucleic acid to hybridize to a specifically referenced nucleic acid sequence under stringent conditions (e.g. Sambrook and Russell, Molecular cloning: A laboratory manual (3 volumes), 2001), it is preferred to analyze and determine the ability of an arbitrary nucleic acid encoding a polypeptide of interest to hybridize to the complementary strand of a nucleic acid sequence encoding the amino acid sequence of formula (I) under stringent conditions by comparing these two nucleotide sequences with alignment tools, such as e.g. the BLASTN (Altschul et al., J. Mol. Biol., 215, 403-410, 1990) and LALIGN alignment tools. Most preferably, the ability of a nucleic acid coding for a polypeptide of interest suspected of being a polypeptide of the invention to hybridize to the complementary strand of a nucleic acid coding for the amino acid sequence of formula (I) is confirmed in a Southern blot assay under the following conditions: 6× sodium chloride/sodium citrate (SSC) at 45° C. followed by a wash in 0.2×SSC, 0.1% SDS at 65° C.

Furthermore, the present invention encompasses polypeptides comprising a fragment, preferably a functional fragment, or functional derivative of any of the above-mentioned inventive amino acid sequences.

Hence, the term "polypeptide or amino acid sequence according to the present invention" also encompasses functional fragments and derivatives of the polypeptide or amino acid sequence of the invention having the property identified above, i.e. binding to IL-17A. A functional derivative of the polypeptide or amino acid sequence of the present invention is meant to encompass any amino acid sequence and/or chemical derivative (non-natural amino acid equivalents, glycosylation, chemical derivation) thereof, that has substantially sufficient accessible amino acid residues or non-natural equivalents to demonstrate binding to IL-17A. In the functional derivative of the polypeptide or amino acid sequence of the invention one or more amino acids may be deleted, modified, inserted and/or substituted. Furthermore, in the context of a "functional derivative", an insertion refers to the insertion of one or more amino acids into the above-described non-derivatized binding proteins. It is preferred with increasing preference that a functional derivative does not comprise more than 5, 4, 3, 2, or nor more than 1 amino acid change(s) (i.e. deleted, modified, inserted and/or substituted amino acids). In another embodiment, it is preferred with increasing preference that not more than 10%, 9%, 8%, 7%, 6%, 5%, 4%, 3%, 2%, or not more than 1% of all amino acids of the polypeptide or amino acid sequence are changed (i.e. are deleted, modified, inserted and/or substituted amino acids). A substitution in a derivative may be a conservative or a non-conservative substitution, but preferably is a conservative substitution. In some embodiments, a substitution also includes the exchange of a naturally occurring amino acid with a non-naturally occurring amino acid. A conservative substitution comprises the substitution of an amino acid with another amino acid having a chemical property similar to the amino acid that is substituted. Preferably, the conservative substitution is a substitution selected from the group consisting of: (i) a substitution of a basic amino acid with a different basic amino acid; (ii) a substitution of an acidic amino acid with a different acidic amino acid; (iii) a substitution of an aromatic amino acid with a different aromatic amino acid; (iv) a substitution of a non-polar, aliphatic amino acid with a different non-polar, aliphatic amino acid; and (v) a substitution of a polar, uncharged amino acid with a different polar, uncharged amino acid. A basic amino acid is selected from the group consisting of arginine, histidine, and lysine. An acidic amino acid is selected from aspartate or glutamate. An aromatic amino acid is selected from the group consisting of phenylalanine, tyrosine and tryptophane. A non-polar, aliphatic amino acid is selected from the group consisting of glycine, alanine, valine, leucine, methionine and isoleucine. A polar, uncharged amino acid is selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v). If a functional derivative comprises a deletion, then in the derivative one or several amino acids that are present in the reference polypeptide have been removed. The deletion should, however, not be so extensive that the derivative comprises less than 3, preferably less than 4, more preferably less than 5 and most preferably less than 6 amino acids in total. As mentioned above, amino acids of the polypeptide or amino acid sequence of the invention may also be modified, e.g. chemically modified. For example, the side chain or a free amino or carboxy-terminus of an amino acid of the polypeptide may be modified by e.g. glycosylation, amidation, phosphorylation, ubiquitination, e.t.c. The chemical modification can also take place in vivo, e.g. in a host-cell, as is well known in the art. For examples, a suitable chemical modification motif, e.g. glycosylation sequence motif present in the amino acid sequence of the polypeptide will cause the polypeptide to be glycosylated. In all embodiments referring to a functional derivative of the invention, it has to be understood that the amino acid sequence having formula (I) as defined herein above is the starting molecule into which the functional derivative is introduced. In the case of a insertion and in two starting molecules having identical sequences with the exception to that in the first molecule $X_a$ equals 4 and in the second molecule $X_a$ equals 5, molecules of identical length and possibly identical amino acid sequence will result, if the insertion into e.g. the C-terminal end of $X_a$ is two amino acids in the first molecule and is one amino acid in the second molecule.

The polypeptides of the present invention bind IL-17A, preferably human IL-17A. Preferably, they bind specifically to IL-17A, i.e. they do not bind to other cytokines or bind these to a much lesser extent, preferably by a factor of at least 2, 5, 10, 50, 100, 500 or 1000 times lower. An exemplary and preferred ELISA assay for determining the binding specificities of polypeptides of the present invention is provided in Examples 6 and 7.

In a preferred embodiment, the polypeptides of the present invention bind human and cynomolgus IL-17A specifically and with high binding affinity.

In further preferred embodiments the polypeptides of the invention have a specific (in vivo and/or in vitro) binding affinity to human IL-17A, preferably with a $K_D$ of $10^{-7}$ to $10^{-12}$ M, more preferably $10^{-8}$ to $10^{-12}$ M, most preferably lower than $10^{-12}$ M. For example and also preferred, the binding affinity of polypeptides of the present invention can be determined according to Example 2 below.

In a most preferred embodiment, the polypeptides of the present invention are selected from the group consisting of SEQ ID NOs: 1 to 119 or a functional derivative thereof as appended to the description.

In a preferred embodiment the polypeptides of the present invention do not only bind but actually inhibit IL-17A (function). This capacity is demonstrated in Examples 3 and 10, where the polypeptides' ability to inhibit the induction of IL-6 in human dermal fibroblasts in response to the addition of IL-17A was demonstrated.

Moreover, the polypeptides of the present invention have high stability in solution, e.g. they are stable at 4° C. for at least 6 months in simple phosphate-buffered saline (see Example 4).

However, stability is not limited to in vitro compositions but has already been proven in mice injected intravenously with a polypeptide of the present invention (see Examples 5 and 12).

In conclusion, the polypeptides of the present invention are well suited for research, diagnostic and medical applications.

Next to substituting IL-17A antibodies they also allow for designing new and less immunogenic fusion proteins for in vivo and in vitro pharmaceutical and diagnostic applications. Hence, in a second aspect, the invention relates to a fusion protein comprising a polypeptide of the invention fused to a pharmaceutically and/or diagnostically active component.

As mentioned, a fusion protein of the invention may comprise non-polypeptide components, e.g. non-peptidic linkers, non-peptidic ligands, e.g. for therapeutically or diagnostically relevant radionuclides.

Preferably, said active component is a cytokine selected from the group consisting of IL-2, IL-12, TNF-alpha, IFN alpha, IFN beta, IFN gamma, IL-10, IL-15, IL-24, GM-CSF, IL-3, IL-4, IL-5, IL-6, IL-7, IL-9, IL-11, IL-13, LIF, CD80, B70, TNF beta, LT-beta, CD-40 ligand, Fas-ligand, TGF-beta, IL-1 alpha and IL-1 beta.

In another preferred embodiment, said active component is a toxic compound, preferably a small organic compound or a polypeptide, more preferably a toxic compound selected from the group consisting of calicheamicin, maytansinoid, neocarzinostatin, esperamicin, dynemicin, kedarcidin, maduropeptin, doxorubicin, daunorubicin, auristatin, Ricin-A chain, modeccin, truncated *Pseudomonas* exotoxin A, diphtheria toxin and recombinant gelonin.

In another preferred embodiment, the fusion protein according to invention is one, wherein said active component is a chemokine, preferably selected from the group consisting of IL-8, GRO alpha, GRO beta, GRO gamma, ENA-78, LDGF-PBP, GCP-2, PF4, Mig, IP-10, SDF-1alpha/beta, BUNZO/STRC33, I-TAC, BLC/BCA-1, MIP-1alpha, MIP-1 beta, MDC, TECK, TARC, RANTES, HCC-1, HCC-4, DC-CK1, MIP-3 alpha, MIP-3 beta, MCP-1-5, Eotaxin, Eotaxin-2, 1-309, MPIF-1, 6Ckine, CTACK, MEC, Lymphotactin and Fractalkine.

In a further preferred embodiment the polypeptide or fusion protein according to the invention contains artificial amino acids.

In further preferred embodiments of the fusion protein of the present invention said active component is a fluorescent dye, preferably a component selected from the groups of Alexa Fluor or Cy dyes (Berlier et al., "Quantitative Comparison of Long-wavelength Alexa Fluor Dyes to Cy Dyes: Fluorescence of the Dyes and Their Bioconjugates", J. Histochem. Cytochem. 51 (12): 1699-1712, 2003.); a photosensitizer, preferably phototoxic red fluorescent protein KillerRed (Bulina et al. (2006) Nat Biotechnol., 24, 95-99) or haematoporphyrin; a pro-coagulant factor, preferably tissue factor; an enzyme for pro-drug activation, preferably an enzyme selected from the group consisting of carboxy-peptidases, glucuronidases and glucosidases; a radionuclide either from the group of gamma-emitting isotopes, preferably $^{99m}$TC, $^{123}$I, $^{111}$In, or from the group of positron emitters, preferably $^{18}$F, $^{64}$Cu, $^{68}$Ga, $^{86}$Y, $^{124}$I, or from the group of beta-emitter, preferably $^{131}$I, $^{90}$Y, $^{177}$Lu, $^{67}$Cu, or from the group of alpha-emitter, preferably $^{213}$Bi, $^{211}$At.

In another preferred embodiment, the polypeptide of the present invention may be directly or via a chemical linker attached to one or more non-polypeptide components as defined herein above.

In a more preferred embodiment of the fusion protein of the present invention said active component is one or more functional Fc domains, preferably one or more human functional Fc domains (see for example SEQ ID NO: 117-119 and SEQ ID NO: 130), which allow(s) for extending the in vivo half-life of the IL-17A binding polypeptides of the invention and some of which direct a mammal's immune response to a site of specific target binding of the inventive polypeptide component of the fusion protein, e.g. in therapeutic, prophylactic and/or diagnostic applications. The polypeptides of the invention can be fused either to the N- or C-terminus of one or more functional Fc domains or to both the N- and the C-terminus of one or more Fc domains. It is preferred that the fusion proteins of the invention comprise multimers, preferably tetramers, trimers or most preferably dimers of the polypeptides of the invention fused to at least one side, preferably to the N-terminus of one or more, preferably one Fc domain. In this respect, it is noted that the Fynomer-Fynomer-Fc fusion protein designated $(2C1)_2$-Fc demonstrates the advantage of multimeric polypeptide-Fc fusions, which have a higher affinity to IL-17A than the corresponding monomeric 2C1-Fc fusion protein, as demonstrated in FIGS. 3e and 3f and Table II of Example 2 below. Hence, a preferred embodiment of the invention is directed to multimeric polypeptide-Fc fusion proteins.

A "functional Fc domain" of an antibody is a term well known to the skilled artisan and defined on the basis of papain cleavage of antibodies. Depending on the amino acid sequence of the constant region of their heavy chains, immunoglobulins are divided in the classes: IgA, IgD, IgE, IgG and IgM, and several of these may be further divided into subclasses (isotypes), e.g. IgG1, IgG2, IgG3, and IgG4, IgA1, and IgA2. According to the heavy chain constant regions the different classes of immunoglobulins are called [alpha], [delta], [epsilon], [gamma], and [mu], respectively. The functional Fc domain of an antibody is directly involved in ADCC (antibody-dependent cell-mediated cytotoxicity) and CDC (complement-dependent cytotoxicity) based on complement activation, C1q binding and Fc receptor binding. The four human IgG isotypes bind different receptors, such as the neonatal Fc receptor, the activating Fc gamma receptors, FcγRI, FcγRIIa, and FcγRIIIa, the inhibitory receptor FcγRIIb, and C1q with different affinities, yielding very different activities. It is known that the affinities to activating and inhibiting receptors of an Fc domain of a human antibody can be engineered and modified (see Strohl W. (2009) Curr Opin Biotechnol, 20, p. 685-691). As mentioned above, the invention therefore comprises Fc fusion(s) which allow(s) for extending the in vivo half-life of the IL-17A binding polypeptides of the invention, and which contains a functional Fc domain from human origin, preferably a human functional Fc domain of an IgG1 antibody (see for example SEQ ID NOs: 117-119 and SEQ ID NO: 130).

In a more preferred embodiment of the fusion protein of the present invention the active component is one or more engineered human functional Fc domains of an IgG1 with activating or silenced effector functions, preferably one or more engineered human functional Fc domains of an IgG1 with silenced effector functions, and most preferably one or more engineered human functional Fc domains of an IgG1 with silenced effector functions with a mutation in L234 and L235

(see for example SEQ ID NOs: 131-135), numbering according to EU index of Kabat (see Johnson G. and Wu T. T. (2000) Nucleic Acids Res. 28, p. 214-218).

A further preferred embodiment relates to polypeptides or fusion proteins according to the invention as mentioned above, further comprising a component modulating serum half-life, preferably a component selected from the group consisting of polyethylene glycol (PEG), immunoglobulin and albumin-binding peptides.

Moreover, it is preferred that the fusion protein of the invention comprises any of the above inventive IL-17A binding polypeptides, preferably those selected from the group consisting of SEQ ID NOs: 117 to 119 and SEQ ID NOs: 130-135 or a functional derivative thereof.

It is noted that the polypeptide or fusion protein of the invention is preferably monomeric but also encompasses multimers, preferably tertramers, more preferably trimers, or most preferably dimers of the inventive polypeptides.

Polypeptides and fusion proteins of the invention may be prepared by any of the many conventional and well known techniques such as plain organic synthetic strategies, solid phase-assisted synthesis techniques or by commercially available automated synthesizers. On the other hand, they may also be prepared by conventional recombinant techniques alone or in combination with conventional synthetic techniques.

In this respect, further aspects of the present invention are directed to (i) a nucleic acid coding for a polypeptide or fusion protein of the invention, (ii) a vector comprising said nucleic acid, and (iii) a host cell comprising said polynucleotide and/or said vector.

Preferably, the invention is directed to an isolated and purified nucleic acid, comprising (i) a nucleic acid encoding for a polypeptide of the invention, preferably encoding the amino acid sequence of formula (I), more preferably (G/E)VTLFVALYDY-$(X)_6$-D-(X)-SFHKGEKF-$(X)_1$-I-$(X)_{5-7}$-G-$(X)_1$-WW-(X)-A-(X)-SLTTG-$X)_{1-2}$-GYIPSNYVAPVDSIQ;

(ii) a nucleic acid having a sequence with at least 60 or 70%, preferably at least 80%, more preferred at least 90%, most preferred at least 95% sequence identity to the nucleic acid sequence of (i);

(iii) a nucleic acid that hybridizes to the complementary strand of a nucleic acid of (i) or (ii);

(iv) a nucleic acid, wherein said nucleic acid is derivable by substitution, addition and/or deletion of one of the nucleic acids of (i), (ii) or (iii);

(v) a fragment of any one of the nucleic acids of (i) to (iv), that hybridizes to the complementary strand of a nucleic acid of (i) coding for a polypeptide according to the invention.

More preferably the nucleic acid of the invention comprises a nucleic acid coding for a polypeptide or fusion protein as described above. In this regard, it is understood that any of the nucleic acids (i) to (v), above, preferably encodes a polypeptide that binds IL-17A and more preferably inhibits IL-17A function.

Nucleic acids of the invention can be DNA, RNA, PNA and any other analogues thereof. The vectors and host cells may be any conventional type that suits the purpose, e.g. production of polypeptides and/or fusion proteins of the invention, therapeutically useful vectors and host cells, e.g. for gene therapy. The skilled person will be able to select those nucleic acids, vectors and host cells from an abundant prior art and confirm their particular suitability for the desired purpose by routine methods and without undue burden.

Preferably the nucleic acid is operably linked to a promoter, preferably linked to a promoter selected from the group of prokaryotic promoters consisting of T5 promoter/lac operator element, T7 promotor/lac operator element, or from the group of eukaryotic promoters consisting of hEF1-HTLV, CMV enh/hFerL promoter.

It is also preferred that a recombinant vector of the invention is one comprising a nucleic acid of the invention and preferably being capable of producing a polypeptide or fusion protein of the invention. Preferably such a vector is selected from the group consisting of pQE vectors, pET vectors, pFUSE vectors, pUC vectors, YAC vectors, phagemid vectors, phage vectors, vectors used for gene therapy such as retroviruses, adenoviruses, adeno-associated viruses.

In addition, the present invention relates to host cells comprising a nucleic acid and/or a vector of the invention.

Furthermore, the present invention encompasses an antibody that specifically binds a polypeptide or fusion protein of the invention. If the antibody binds to the fusion protein, it specifically binds to the portion thereof consisting of the polypeptide of the invention or an fusion epitope, i.e. the binding site of an antibody partially consisting of the polypeptide of the invention and partially consisting of a pharmaceutically and/or diagnostically active component, which is preferably a polypeptide or peptide. The antibodies may be polyclonal or monoclonal antibodies. As used herein, the term “antibody” refers not only to whole antibody molecules, but also to antigen-binding fragments, e.g., Fab, $F(ab')_2$, Fv, and single chain Fv fragments. Also included are chimeric antibodies, preferably humanized antibodies. Such antibodies are useful as research tools for distinguishing between arbitrary proteins and polypeptides of the invention. A further aspect relates to a hybridoma cell line, expressing a monoclonal antibody according to the invention.

Because the polypeptides and fusion proteins of the present invention demonstrate IL-17A-binding and inhibitory properties as well as storage and in vivo stability, a further aspect of the present invention relates to a pharmaceutical composition comprising a polypeptide or fusion protein, a nucleic acid and/or a recombinant vector of the invention and optionally a pharmaceutically acceptable carrier. The term pharmaceutical composition is meant to also encompass diagnostic compositions for in vivo use.

Pharmaceutical compositions of the invention may be manufactured in any conventional manner. In effecting treatment of a subject suffering from the diseases indicated below, at least one compound of the present invention can be administered in any form or mode which makes the therapeutic polypeptide or therapeutic fragment thereof bioavailable in an effective amount, including oral or parenteral routes. For example, compositions of the present invention can be administered subcutaneously, intramuscularly, intravenously, by inhalation and the like. One skilled in the art in the field of preparing formulations can readily select the proper form and mode of administration depending upon the particular characteristics of the product selected, the disease or condition to be treated, the stage of the disease or condition and other relevant circumstances (see. e.g. Remington’s Pharmaceutical Sciences, Mack Publishing Co. (1990)). A suitable carrier or excipient may be a liquid material which can serve as a vehicle or medium for the active ingredient. Suitable carriers or excipients are well known in the art and include, for example, stabilizers, antioxidants, pH-regulating substances, controlled-release excipients, etc. A composition according to the invention is preferably provided in lyophilized form.

For immediate administration it is dissolved in a suitable aqueous carrier, for example sterile water for injection or sterile buffered physiological saline. If it is desirable to produce larger volumes for administration by infusion rather than as a bolus injection, it is advantageous to incorporate human serum albumin or the patient's own heparinised blood into the solvent at the time of final formulation. Alternatively, the formulation can be administered subcutaneously. The presence of an excess of a physiologically inert protein such as human serum albumin prevents loss of the pharmaceutically effective polypeptide by adsorption onto the walls of the container and tubing used for the infusion solution. If albumin is used, a suitable concentration is from 0.5 to 4.5% by weight of the saline solution.

The IL-17A-binding and inhibiting polypeptides of the invention are particularly useful for the treatment and/or prevention of IL-17A- and/or Th17-related diseases or medical conditions. Hence, a further aspect of the present invention is directed to the use of a polypeptide or fusion protein, a nucleic acid and/or a recombinant vector of the invention for medical use, i.e. for the preparation of a medicament, preferably for treating and/or preventing a disease or medical condition, preferably selected from the group consisting of IL-17A and/or Th17-related diseases or medical conditions.

In a preferred embodiment, the medical use of the invention relates to treating and/or preventing of diseases or medical conditions selected from inflammatory, autoimmune and/or bone loss-related diseases and conditions.

In a most preferred embodiment, said inflammatory, autoimmune and/or bone loss-related diseases and conditions are selected from arthritis, preferably rheumatoid arthritis, arthritis chronica progrediente, reactive arthritis, psoriatic arthritis, enteropathic arthritis and arthritis deformans, rheumatic diseases, spondyloarthropathies, ankylosing spondylitis, Reiter syndrome, hypersensitivity (including both airways hypersensitivity and dermal hypersensitivity), allergies, systemic lupus erythematosus, inflammatory muscle disorders, polychondritis, sclerodoma, Wegener granulomatosis, dermatomyositis, Steven-Johnson syndrome, chronic active hepatitis, myasthenia gravis, psoriasis, idiopathic sprue, autoimmune inflammatory bowel disease, ulcerative colitis, Crohn's disease, Irritable Bowel Syndrome, endocrine ophthalmopathy, Graves disease, sarcoidosis, ischemia, systemic sclerosis, multiple sclerosis, primary biliary cirrhosis, juvenile diabetes (diabetes mellitus type I), autoimmune haematological disorders, hemolytic anaemia, aplastic anaemia, pure red cell anaemia, idiopathic thrombocytopenia, uveitis (anterior and posterior), keratoconjunctivitis sicca, vernal keratoconjunctivitis, interstitial lung fibrosis, glomerulonephritis (with and without nephrotic syndrome), idiopathic nephrotic syndrome or minimal change nephropathy, tumors, inflammatory disease of skin inflammation, cornea inflammation, myositis, loosening of bone implants, acute transplant rejection, metabolic disorders, atherosclerosis, diabetes, and dislipidemia, bone loss, osteoarthritis, osteoporosis, periodontal disease of obstructive or inflammatory airways diseases, asthma, bronchitis, pneumoconiosis, pulmonary emphysema, acute and hyperacute inflammatory reactions, diseases involving IL-17A-mediated TNF-alpha, acute infections, septicemia, septic shock, endotoxic shock, adult respiratory distress syndrome, meningitis, pneumonia, severe burns, cachexia, wasting syndrome, stroke, herpetic stromal keratitis and dry eye disease. All of the above specified diseases and medical conditions have in common that their origin and/or symptom(s) are IL-17A- and/or Th-17-related.

The amount and mode of administration of the inventive compounds, i.e. polypeptides, fusion proteins, nucleic acids, vectors, and host cells for treating and/or preventing a disease or medical condition, preferably selected from the group consisting of IL-17A- and/or Th17-related diseases or medical conditions, more preferably those specifically listed above, will, of course, vary depending upon the particular polypeptide or fusion protein inhibitor of the invention, the individual patient group or patient, the presence of further medically active compounds and the nature and severity of the condition being treated. However, it is presently preferred that for prophylactic and/or therapeutic use dosages of about 0.01 mg to about 20 mg per kilogram body weight, preferably about 0.1 mg to about 5 mg per kilogram body weight should be administered. Preferably, the frequency of administration for prophylactic and/or therapeutic uses lies in the range of about twice per week up to about once every 3 months, preferably about once every 2 weeks up to about once every 10 weeks, more preferably once every 4 to 8 weeks. IL-17A-binding polypeptides and fusion proteins of the Invention are conveniently and preferably administered parenterally, intravenously, preferably into the antecubital or other peripheral vein, intramuscularly or subcutaneously. IL-17A-binding polypeptides can also be delivered topically as eye drops. A preferred prophylactic and/or therapeutic treatment of a patient involves the administration of polypeptides of the invention once per month to once every 2 to 3 months or less frequently.

In consequence, the present invention also relates to a method of treatment, wherein a pharmacologically effective amount of the above pharmaceutical composition is administered to a patient in need thereof, preferably a patient suffering from IL-17A- and/or Th17-related diseases or medical conditions, more preferably one of the above specified diseases or medical conditions. The term "treatment" as used herein relates to the prophylactic and/or therapeutic treatment of a disease or medical condition.

The IL-17A-binding polypeptides and fusion proteins of the invention may be administered as the sole active ingredient or in conjunction with, e.g. as an adjuvant to or in combination with, other drugs, e.g. immunosuppressive or immune modulating agents or other anti-inflammatory agents, e.g. for the treatment or prevention of diseases mentioned above. For example, the IL-17A-binding polypeptides and fusion proteins of the invention may be used in combination with immunosuppressive monoclonal antibodies, e.g. monoclonal antibodies with affinity to leukocyte receptors, e.g. MHC, CD2, CD3, CD4, CD7, CD8, CD25, CD28, CD40, CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (e.g. designated ATCC 68629) or a mutant thereof, e.g. LEA29Y; adhesion molecule inhibitors, e.g. LFA-I antagonists, ICAM-I or -3 antagonists, VCAM-4 antagonists or VLA-4 antagonists. In addition, the polypeptides and fusion proteins of the invention may be used in combination with DMARD, e.g. Gold salts, sulphasalazine, anti-malarias, methotrexate, D-penicillamine, azathioprine, mycophenolic acid, cyclosporine A, tacrolimus, sirolimus, minocycline, leflunomide, glucocorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CCI779, ABT578, AP23573 or TAFA-93; an ascomycin having immuno-suppressive properties, e.g. ABT-281, ASM981, etc.; corticosteroids; cyclophosphamide; azathioprene; methotrexate; leflunomide;

mizoribine; mycophenolic acid; mycophenolate mofetil; 15-deoxyspergualine or an immuno-suppressive homologue, analogue or derivative thereof; or a chemotherapeutic agent, e.g. paclitaxel, gemcitabine, cisplatinum, doxorubicin or 5-fluorouracil; anti-TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL-1 blockers, e.g. Anakinra or IL-1 trap, AAL160, ACZ 885, IL-6 blockers; inhibitors or activators of proteases, e.g. metalloproteases, anti-IL-15 antibodies, anti-IL-6 antibodies, anti-IL-23 antibodies, anti-IL-22 antibodies, anti-IL-21 antibodies, anti-IL-12 antibodies, anti-IFN-gamma antibodies, anti-IFN-alpha antibodies, anti-CD20 antibodies, NSAIDs, such as aspirin or an anti-infectious agent. Naturally, this list of agents for co-administration is not limiting nor complete.

The invention is further described by way of illustration in the following examples, none of which are to be interpreted as limiting the scope of the invention as outlined in the appended claims.

FIGURES

FIG. 1. shows the SDS PAGE analysis of embodiments of IL-17-binding polypeptides of the invention: (a) SDS PAGE of B1_2 (SEQ ID No: 39) (lane 1), E4 (SEQ ID NO: 57) (lane 2), 2C1 (SEQ ID NO: 107) (lane 3), E4-Fc (SEQ ID NO: 117) (lane 4: non-reducing conditions, lane 5: reducing conditions), 2C1-Fc (SEQ ID NO: 118) (lane 6: non-reducing conditions, lane 7: reducing conditions); (b) SDS PAGE of [(2C1)2-Fc] (SEQ ID NO: 119) (lane 1: non-reducing conditions, lane 2: reducing conditions). The molecular weight of (2C1)2-Fc is estimated from the reference molecular weight full range marker (not shown).

Figure 4:
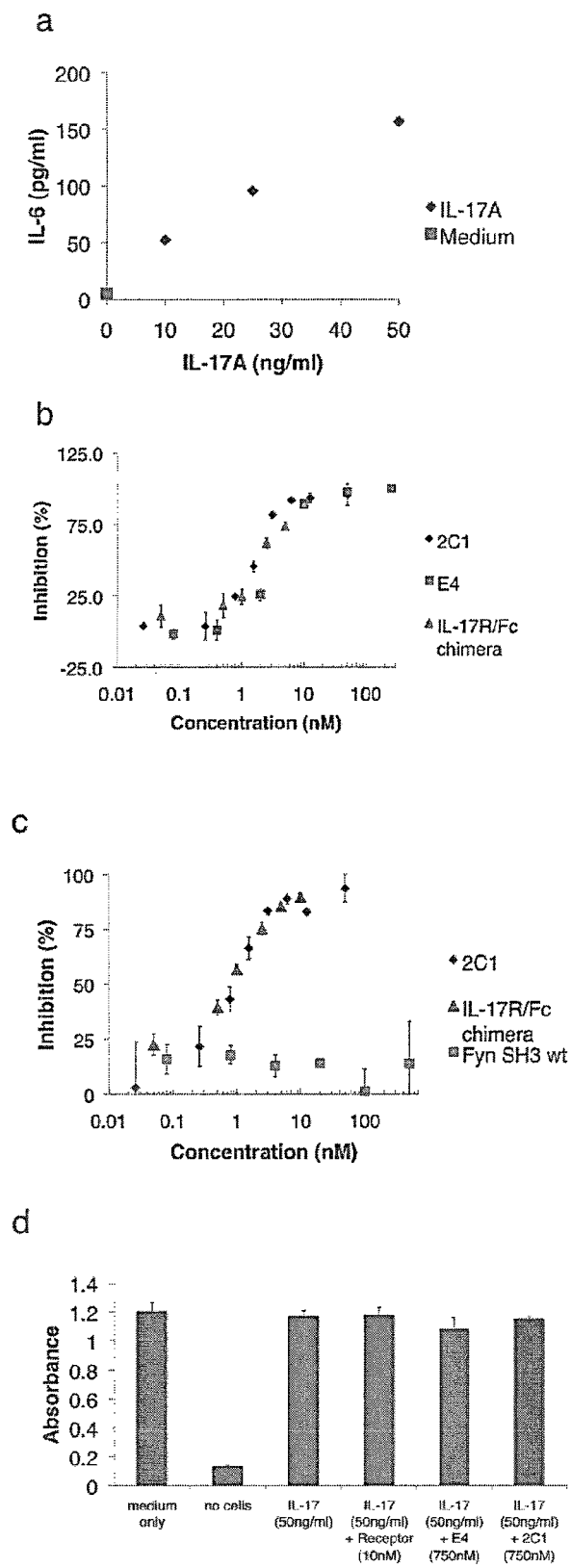

FIG. 4 depicts the results of an IL-17A inhibition cell assay: (a) Dose-dependent induction of IL-6 after incubation of NHDF cells with IL-17A. (b) Dose-dependent inhibition of IL-17A-induced IL-6 production in NHDF cells by Fyn SH3 derived IL-17 binders and IL-17A receptor-Fc chimera. (c) same as b), Fyn SH3 wt protein was used as a control protein with no IL-17A binding affinity. (d) XTT-assay: viable cells are able to metabolize the tetrazolium salt XTT to a coloured product. In our experiment, all cells were viable after 24 hours incubation with IL-17A, IL-17A and Fyn SH3 binders, or IL-17A and IL-17R-Fc chimera.

Figure 5:
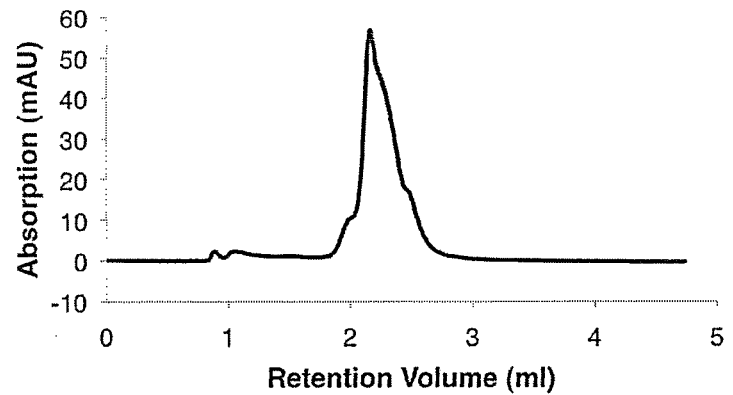

FIG. 5 depicts a size exclusion chromatography with an IL-17A-binding polypeptide of the invention designated G3 (SEQ ID NO: 34) one day after purification (stored in PBS at 4° C.). The chromatography was performed using a Superdex 75 (GE Healthcare) column.

Figure 6A:
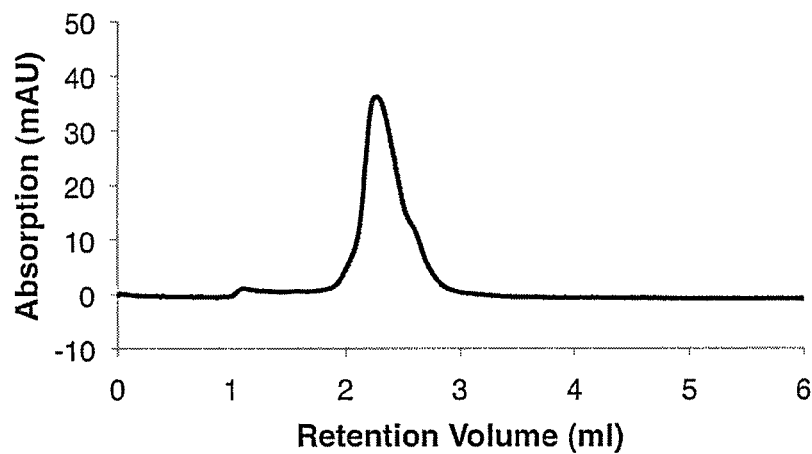
Figure 6B:
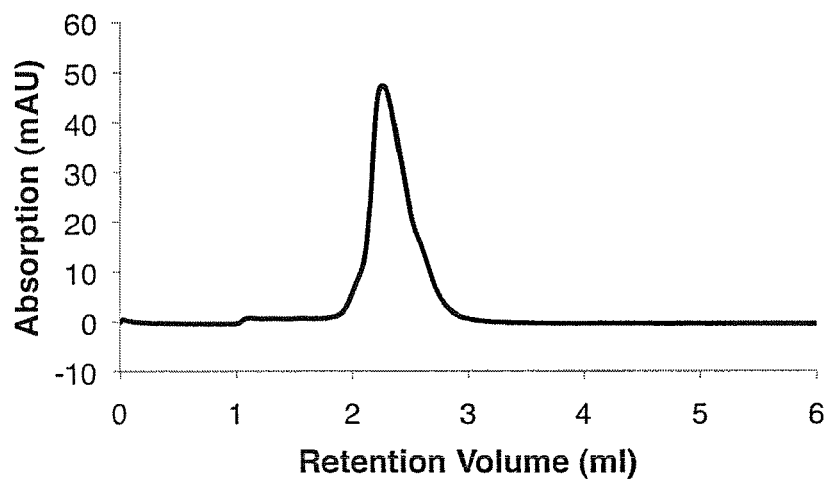

FIG. 6 depicts a size exclusion chromatography with an IL-17A-binding polypeptide of the invention designated G3 (SEQ ID NO: 34) stored for more than six months at 4° C. (a) and −20° C. (b).

Figure 7A:
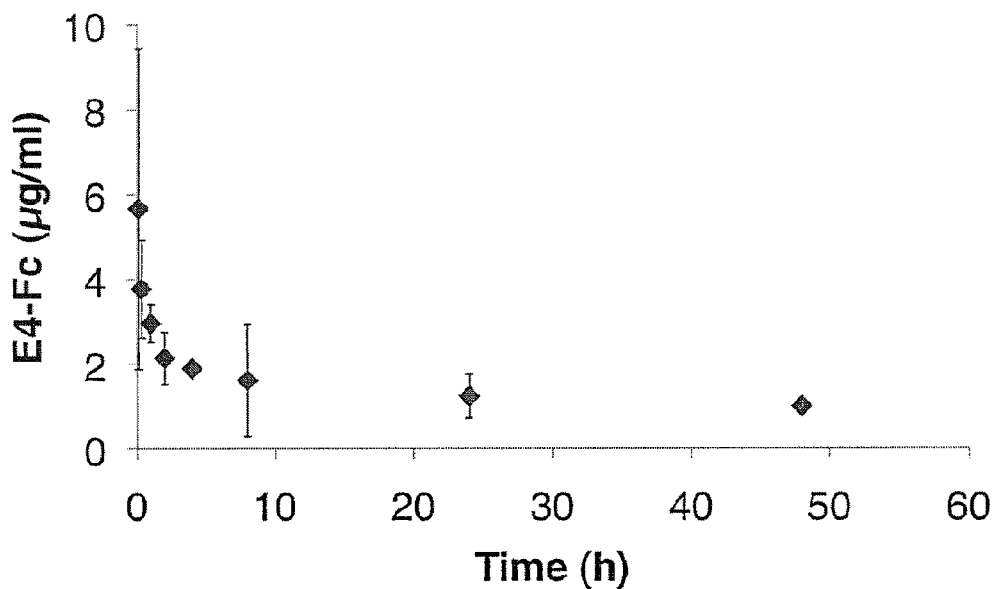
Figure 7B:
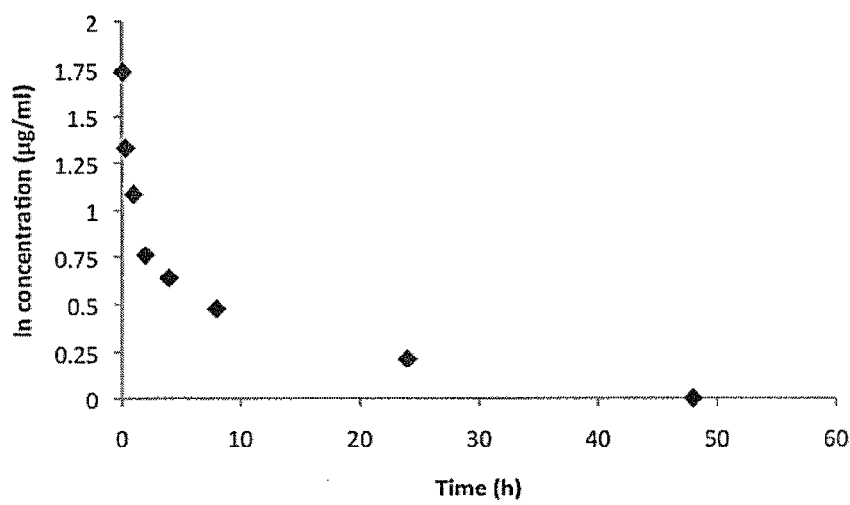

FIG. 7 shows the pharmacokinetic data of an IL-17A-binding polypeptide of the invention designated E4-Fc (SEQ ID NO: 117) in mice: (a) E4-Fc concentration in serum is plotted versus time after intravenous injection, (b) same as (a), but with a semi-logarithmic display. The last four time points were used to calculate the terminal half-life of 50.6 hours.

Figure 8:
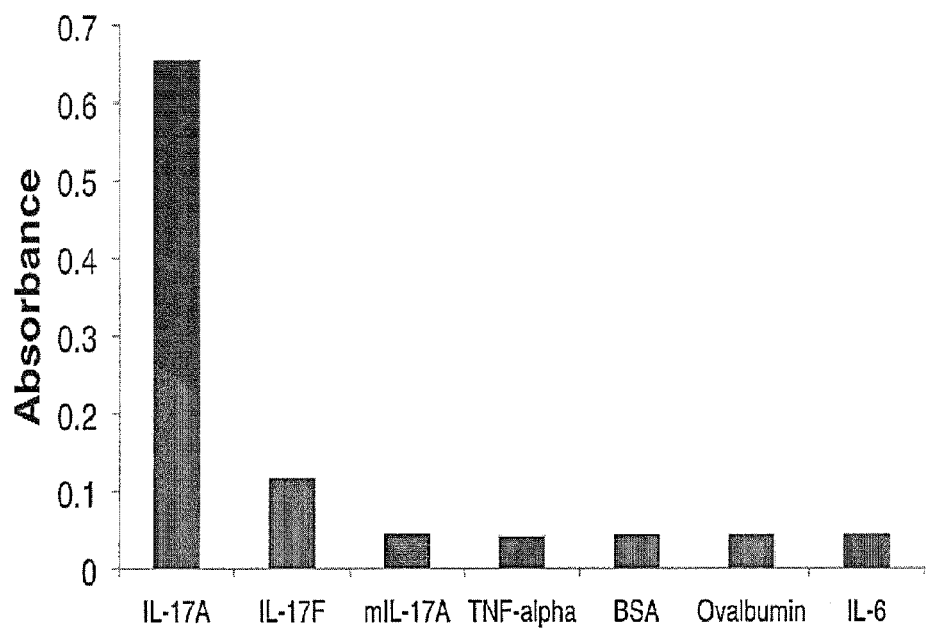

FIG. 8 shows a table of the binding specificity of a polypeptide of the invention designated 2C1 (SEQ ID NO: 107). The absorbance results relate to an ELISA performed using different target proteins: human IL-17A, human IL-17F, mIL-17A (murine IL-17 A), TNF-alpha (human tumor necrosis factor alpha), BSA (bovine serum albumin), Ovalbumin (hen egg white), IL-6 (human interleukin 6).

Figure 9:
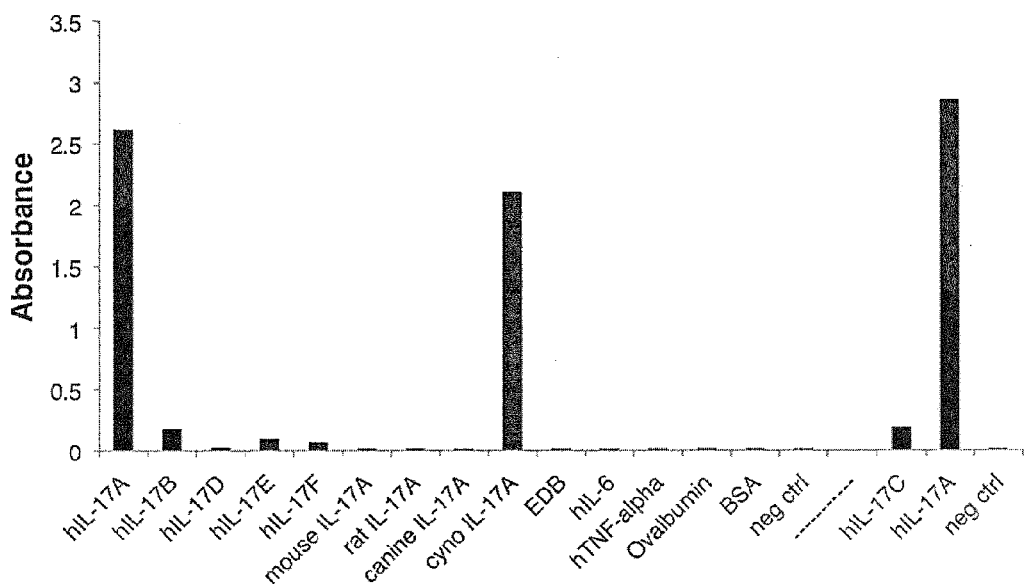

FIG. 9 shows the specificity of the Fyn SH3-derived polypeptide of the invention 2C1 (SEQ ID NO: 107). Different IL-17 family members, IL-17A of different species and other unrelated antigens were used in ELISA with the Fyn SH3-derived polypeptide of the invention 2C1 (SEQ ID NO: 107) as binding agent. Fyn SH3-derived polypeptide of the invention 2C1 (SEQ ID NO: 107) only binds to human and cynomolgus IL-17A. No binding to any of the other antigens could be detected. On the right side of the Figure (right side of the dashed line) the ELISA signal to human IL-17C is shown, which was determined on another day with the human IL-17A control. Legend: hIL-17A: human Interleukin 17A, hIL-17B: human Interleukin 17B, hIL-17D: human Interleukin 17D, hIL-17E: human Interleukin 17E, hIL-17F: human Interleukin 17F, mouse IL-17A: mouse Interleukin 17A, rat IL-17A: rat Interleukin 17A, canine IL-17A: canine Interleukin 17A, cyno II-17A: cynomolgus Interleukin 17A, EDB: extra domain B of fibronectin, hIL-6: human Interleukin 6, hTNF alpha: human Tumor Necrosis Factor alpha, Ovalbumin: Albumin from chicken egg white, BSA: Bovine Serum Albumin neg ctrl: no antigen was used for coating, hIL-17C: human Interleukin 17C.

Figure 10:
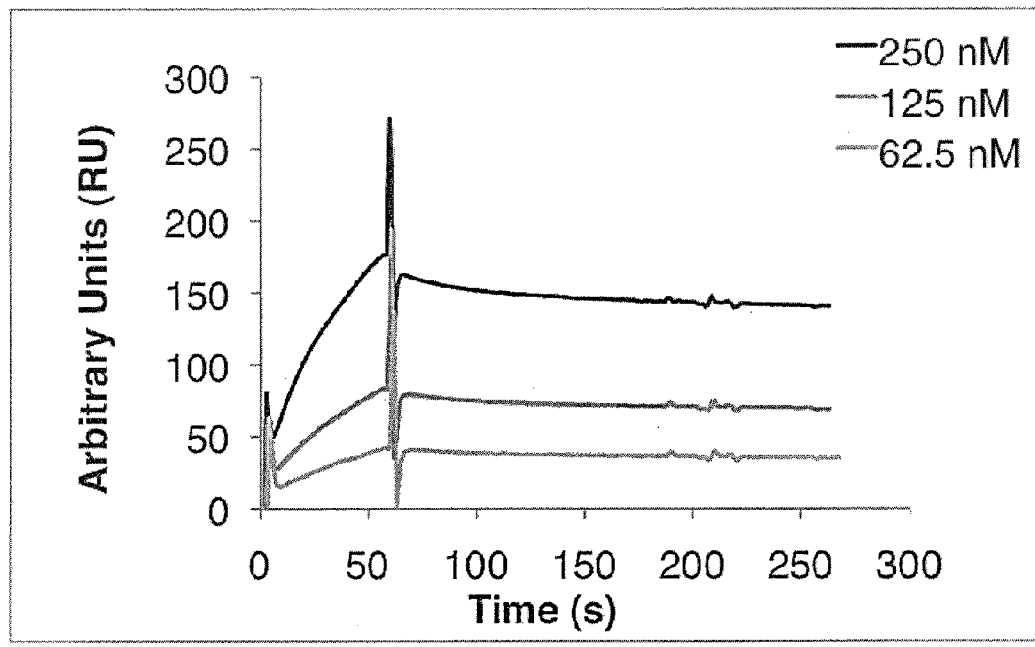

FIG. 10 depicts the Biacore sensogram of the Fyn SH3-derived polypeptide of the invention 2C1 (SEQ ID NO: 107) on a chip coated with cynomolgus IL-17A refolded from inclusion bodies.

Figure 11:
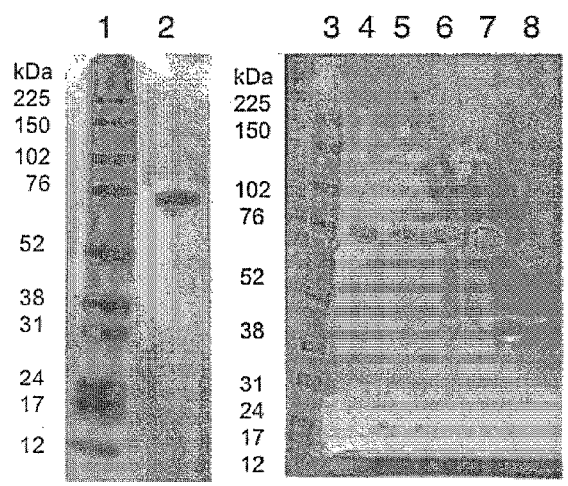

FIG. 11 shows SDS PAGE analysis of Fc fusion proteins. Lane 1: full range rainbow marker (GE Healthcare), lane 2: 2C1-Fc (SEQ ID NO: 130), lane 3: full range rainbow marker (GE Healthcare), lane 4: 2C1-m5-Fc(LALA) (SEQ ID NO: 133), lane 5: 2C1-m10-Fc(LALA) (SEQ ID NO: 134), lane 6: 2C1-m15-Fc(LALA) (SEQ ID NO: 135), lane 7: 2C1-m5E-Fc(LALA) (SEQ ID NO: 132), lane 8: 2C1-Fc(LALA) (SEQ ID NO: 131).

Figure 12:
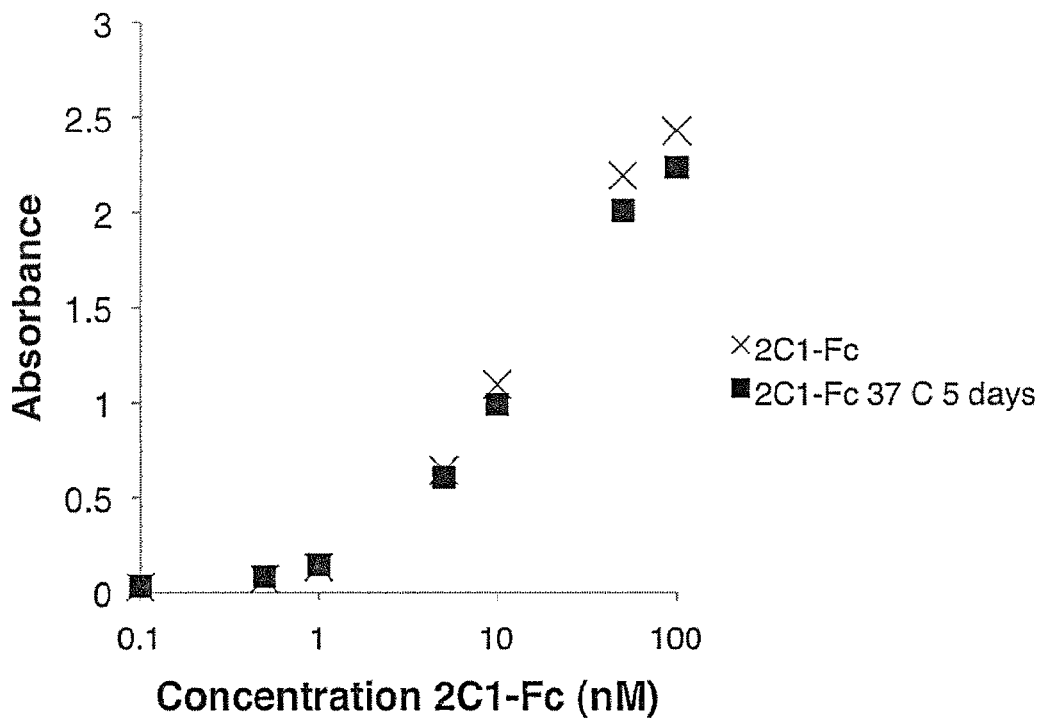

FIG. 12 shows the ELISA of 2C1-Fc (SEQ ID NO: 130) binding to IL-17A after storage for 5 days at 37° C. in human serum (■) compared to the standard control 2C1-Fc (SEQ ID NO: 130) stored at 4° C. in PBS (x).

Figure 13:
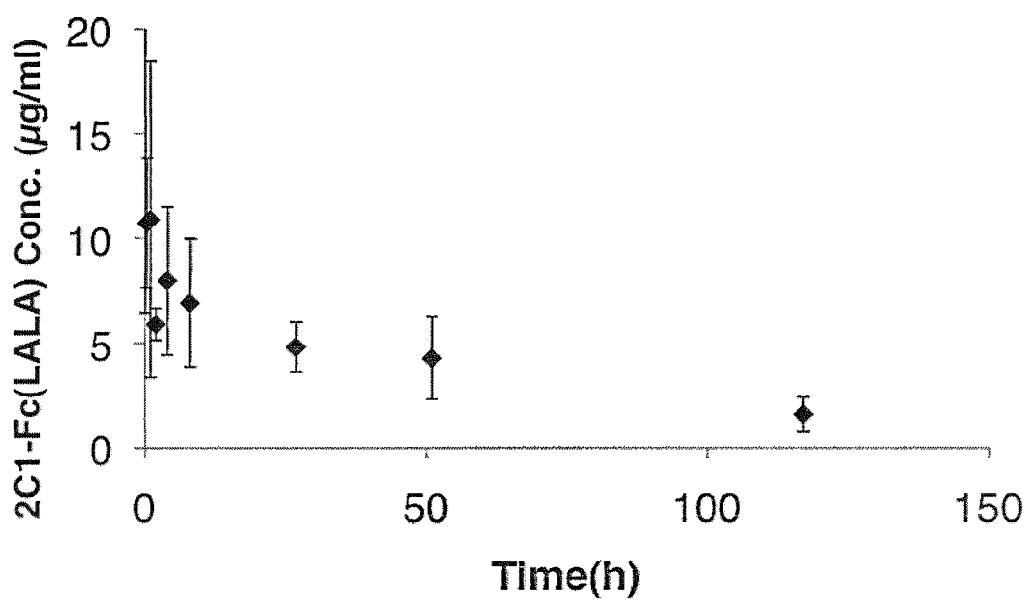

FIG. 13 shows the serum concentration at different timepoints of 2C1-Fc(LALA) (SEQ ID NO: 131) after a single i.v. injection into mice. 2C1-Fc(LALA) fusion protein (SEQ ID NO: 131) produced in mammalian cells was injected (40 µg per animal) intravenously (iv) (n=5) in mice. The last four time points of the PK profile were used to calculate a terminal half-life of 2C1-Fc fusion protein of 53 hours.

Figure 14:
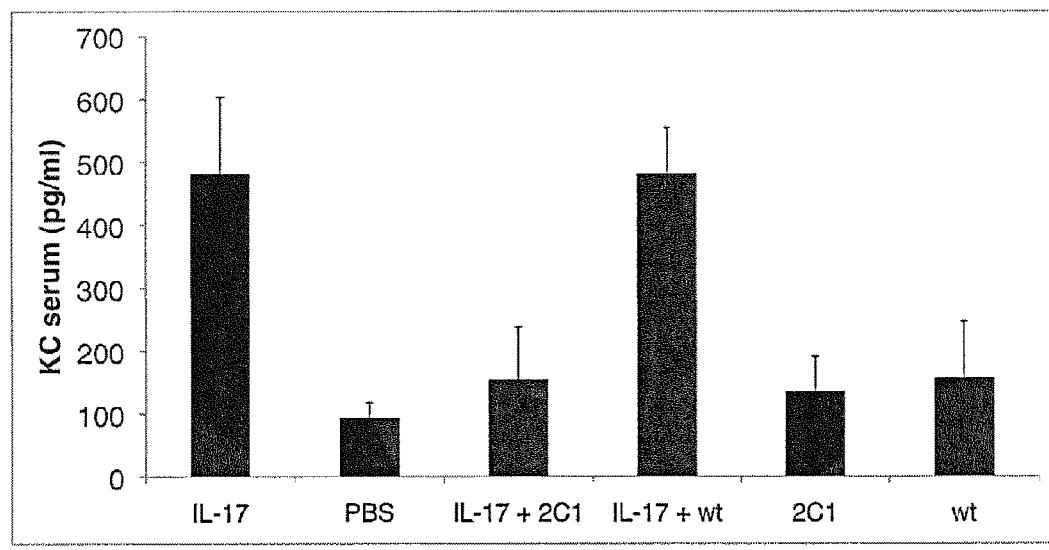

FIG. 14 shows the inhibition of human IL-17A induced KC production by the anti-IL-17 Fyn SH3-derived polypeptide 2C1 (SEQ ID NO: 107) of the invention in an acute inflammation model. Two hours after s.c. injection of either 3 µg human IL-17A (IL-17), PBS (PBS), 3 µg human IL-17A with 17 µg monomeric Fyn SH3-derived polypeptide 2C1 (SEQ ID NO: 107) of the invention (1-17+2C1), 3 µg human IL-17A with 16 µg wild-type Fyn SH3 monomer (IL-17+wt), 17 µg monomeric Fyn SH3-derived polypeptide 2C1 (SEQ ID NO: 107) of the invention alone (2C1), or 16 µg wild-type Fyn SH3 monomer alone (wt), blood samples were taken and KC levels in mouse-serum were quantified. Mean KC levels of 4 mice per group are shown (±SD), with the exception of the wild-type control groups (Fyn SH3 without and with IL-17A), where mean levels of 3 mice are shown (±SD).

Figure 15:
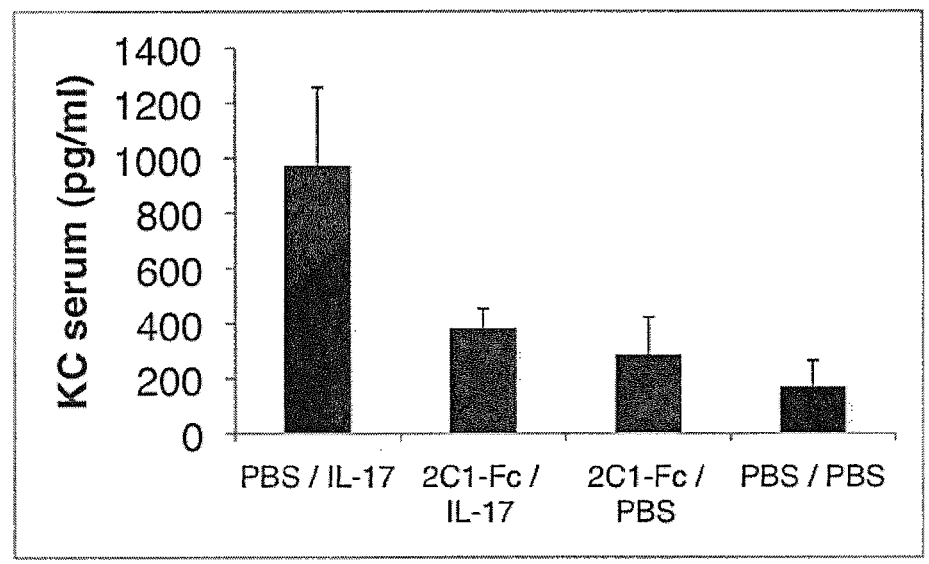

FIG. 15 depicts the inhibition of human IL-17A induced KC production by 2C1-Fc fusion protein (SEQ ID NO: 130) in an acute inflammation model. 2C1-Fc/IL-17: 44 µg of 2C1-Fc (SEQ ID NO: 130) was injected i.v. followed by s.c. injection of 3 µg human IL-17A. Two hours after administration of IL-17A, blood samples were taken from the mice and KC serum levels were measured by ELISA. Control experiments were performed as follows: PBS/IL-17: i.v. injection of PBS followed by s.c. injection of IL-17; 2C1-Fc/PBS: i.v. injection of 2C1-Fc (SEQ ID NO: 130) followed by s.c. injection of PBS; PBS/PBS: i.v. injection of PBS followed by s.c. injection of PBS;. Mean KC levels of 3-5 mice per group are shown (±SD).

EXAMPLES

Example 1

Fyn SH3-Derived Polypeptides of the Invention Bind to IL-17A as Determined by Monoclonal Phage ELISA Methods DNA encoding the amino acid sequences shown in SEQ ID NOs: 1 to 116 were cloned into the phagemid vector pHEN1 as described for the FYN SH3 library in Grabulovski et al. (Grabulovski et al. (2007) JBC, 282, p. 3196-3204). Phage production was performed according to standard protocols (Viti, F. et al. (2000) Methods Enzymol. 326, 480-505). Monoclonal bacterial supernatants containing phages were used for ELISA: biotinylated IL-17A (purchased from R&D Systems, biotinylation was performed with NHS-PEO4-biotin (Pierce) according to the manufacturer's instructions) was immobilized on streptavidin-coated wells (StreptaWells, High Bind, Roche), and after blocking with PBS, 2% milk (Rapilait, Migros, Switzerland), 20 µl of PBS, 10% milk and 80 µl of phage supernatants were applied. After incubating for 1 h and washing, bound phages were detected with anti-M13-HRP antibody conjugate (GE Healthcare). The detection of peroxidase activity was done by adding BM blue POD substrate (Roche) and the reaction was stopped by adding 1 M $H_2SO_4$. The DNA sequence of the binders was verified by DNA sequencing (BigDye Terminator v3.1 cycle sequencing kit, ABI PRISM 3130 Genetic Analyzer, Applied Biosystems).

Results

The amino acid sequences of Fyn SH3-derived IL-17A binders is presented in SEQ ID NOs: 1 to 116 as appended in the sequence listing.

Example 2

Fyn SH3-Derived Polypeptides of the Invention Bind to Recombinant Human IL-17 a with High Affinities This example shows the cloning and expression of different formats of Fyn SH3-derived IL-17A-binding polypeptides, as well as the characterization of these polypeptides by size exclusion chromatography and surface plasmon resonance experiments.

a) Cloning and expression of Fyn SH3-derived IL-17A-binding polypeptides

Selected Fyn SH3-derived IL-17A-binding polypeptides (clone B1_2: SEQ ID NO: 39, clone E4: SEQ ID NO: 57 and clone 2C1: SEQ ID NO:107) were cloned into the cytosolic expression vector pQE-12 and expressed as well as purified as described in Grabulovski et al. (Grabulovski et al. (2007) JBC, 282, p. 3196-3204).

b) Cloning and expression of Fyn SH3-derived IL-17A-binding polypeptides fused to the Fc part of a human IgG1 antibody Clones E4 and 2C1 (SEQ ID NO: 57 and SEQ ID NO:107) were cloned and expressed as fusion proteins with the Fc part of a human IgG1 antibody (see below for procedure; SEQ ID NO: 117 and 118). Furthermore, a 2C1 dimer with a 10 amino acid linker [(2C1)$_2$-Fc] was cloned and expressed as Fc fusion protein (SEQ ID NO: 119).

The Fc part of human IgG1 was PCR-amplified using the primers fm5 (5' ATCGGGATCCGACAAAACTCACACAT-GCC 3', SEQ ID NO: 121) and fm6 (5' TAC-GAAGCTTTCATTTACCCGGAGACAGGG 3', SEQ ID NO: 122) and using the commercial pFUSE-hIgG1-Fc2 (Invivogen) eukaryotic vector as template. The resulting PCR product was digested with BamHI/HindIII and ligated with the pASK-IBA2 vector (IBA-Biotagnology) previously digested with the same enzymes, yielding the new vector pAF.

The genetic information of clones E4 and 2C1 (SEQ ID NO: 57 and SEQ ID NO:107) was PCR amplified with fm7 (5' ATATCACCATGGGGCCGGAGTGA-CACTCTTTGTGGCCCTTTATG 3', SEQ ID NO: 123) and fm8 (5' CGTAGGA-TCCCTGGATAG-AGTCAACTG-GAGC 3', SEQ ID NO: 124). For the preparation of the 2C1 dimer fused to Fc, the 2C1 DNA template was used for two independent PCRs. In the first reaction the primers 47b.fo (5' AGA GCC ACC TCC GCC TGA ACC GCC TCC ACC CTG GAT AGA GTC AAC TGG AGC CAC 3', SEQ ID NO: 125) and 52. ba (5' GAC TAA CGA GAT CGC GGA TCC GGA GTG ACA CTC TTT GTG GCC CTT TAT 3', SEQ ID NO: 126) were used and in the second PCR primers 48b.ba (5' GGT GGA GGC GGT TCA GGC GGA GGT GGC TCT GGA GTG ACA CTC TTT GTG GCC CTT TAT 3', SEQ ID NO: 127) and 51. fo (5' ATC CCA AGC TTA GTG ATG GTG ATG GTG ATG GAG ATC CTC TTC TGA GAT GAG TTT TTG TTC ACC CTG GAT AGA GTC AAC TGG AGC CAC 3', SEQ ID NO: 128) were used.

The two DNA fragments were assembled by PCR, yielding a 2C1 homodimer with a 10 amino acid linker (GGGGSGGGGS, SEQ ID NO: 120) between the two domains. The resulting DNA fragment was further amplified as described for the 2C1 monomer using the primers fm7 and fm8. Obtained PCR products were then digested with NcoI/BamHI and cloned into the double-digested periplasmic expression vector pAF. Plasmids were electroporated into *E. coli* TG1 and protein expression was induced with 0.2 µg/ml anhydrotetracyclin. Bacterial cultures were grown overnight at 25° C. in a rotary shaker and Fynomer-Fc fusion proteins were purified from the periplasmic fraction in a single protein A-affinity chromatography step. SDS PAGE (Invitrogen) analysis was performed with 20 µl of protein solution.

c) Size Exclusion Chromatography (SEC)

Size Exclusion Chromatography (SEC) was performed on an ÄKTA FPLC system using a Superdex 75 column (10/300) or Superdex 75 Short Column (5/150) (GE Healthcare).

d) Affinity Measurements

Affinity measurements were performed using a BIAcore 3000 instrument (Biacore). For the interaction analysis between biotinylated IL-17A and monomeric Fyn SH3-derived IL-17A-binding polypeptides, and between biotinylated IL-17A and E4-Fc (SEQ ID NO: 117), a streptavidin SA chip (Biacore) was used with 1300 and 510 RU biotinylated IL-17A immobilized, respectively. The running buffer was PBS, 0.1% NaN$_3$ and surfactant P20 (Biacore). The interactions were measured at a flow of 20 µl/min and injection of different concentrations of Fyn SH3-derived IL-17A-binding polypeptides. For the interaction analysis between IL-17A and the 2C1-Fc fusions as well as the (2C1)$_2$-Fc fusion, a CM5 chip (Biacore) was coated with 2900 RU goat anti-human IgG Fc-specific antibody (Jackson Immunoresearch). The running buffer was HBS-EP (Biacore). The interactions were measured by injecting about 250 to 275 RU Fc fusion protein at a flow rate of 10 µl/min, followed by injection of different concentrations of IL-17A (R&D Systems) at a flow rate of 30 µl/min. All kinetic data of the interaction (separate kon/koff) were evaluated using BIA evaluation 3.2RC1 software.

e) Results

The expression yields for monomeric Fyn SH3-derived IL-17A-binding polypeptides of the invention ranged from 60 to 85 mg/liter of bacterial culture under non-optimized conditions in shake flasks. The Fc-fusion proteins were expressed with a yield of 0.2 to 0.4 mg/liter (Table I). The Fc-fusion proteins have the sequences listed in SEQ ID NOs: 117 to 119 as appended)

TABLE I

Expression yields after purification of bacterial culture under non-optimized conditions in shake flasks in *E. coli*.

| Clone | SEQ ID NO: | Expression yield (mg/L) |
|---|---|---|
| B1_2 | 39 | 65 |
| E4 | 57 | 85 |
| 2C1 | 107 | 60 |
| E4-Fc | 117 | 0.4 |
| 2C1-Fc | 118 | 0.3 |
| [(2C1)$_2$-Fc] | 119 | 0.2 |

Figure 1:
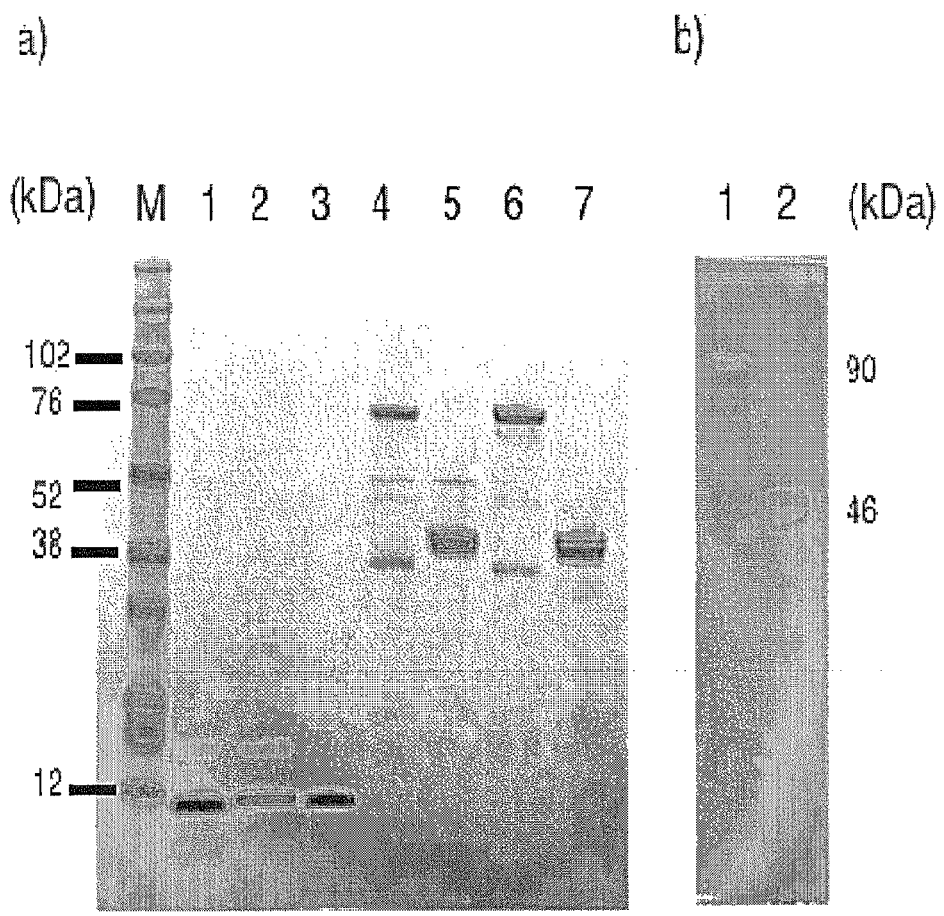

FIG. 1 shows the SDS PAGE analysis of the indicated purified proteins.

Figure 2:
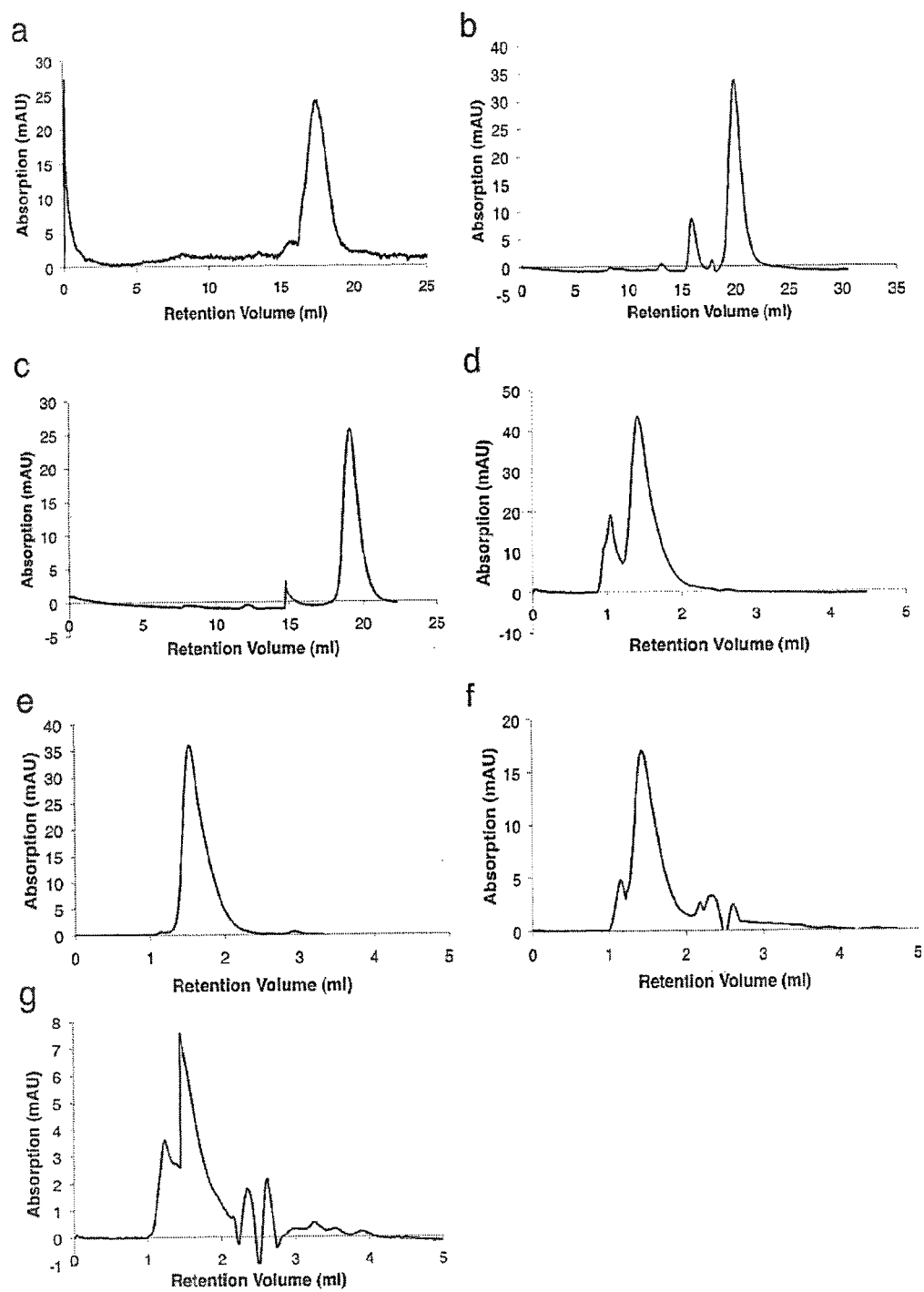
FIG. 2 shows size exclusion chromatograms (SEC) of IL-17A-binding polypeptides of the invention: (a) Clone B1_2 (SEQ ID NO: 39), (b) E4 (SEQ ID NO: 57), (c) 2C1 (SEQ ID NO: 107), (d) E4-Fc (SEQ ID NO: 117), (e) SEC-peak purified E4-Fc, analyzed after 40 days after purification and storage in PBS at 4° C., (f) 2C1-Fc (SEQ ID NO: 118), (g) (2C1)2-Fc (SEQ ID NO: 119).

Size exclusion chromatography (SEC) profiles demonstrated that all constructs eluted mainly as single, monomeric peaks (see FIG. 2). As already observed in earlier studies for Fyn SH3-derived binding proteins (Grabulovski et al. (2007) JBC, 282, p. 3196-3204), the main peak elutes later than expected for a protein of about 8 kDa. For the Fc-fusion proteins of the invention a second purification step by size exclusion chromatography was performed after the single-step protein A-sepharose purification yielding monomeric proteins as shown for the fusion protein E4-Fc (SEQ ID NO: 117) in FIG. 2e. E4-Fc (SEQ ID NO: 117) was stable for at least 40 days when stored at 4° C. in PBS.

Figure 3:
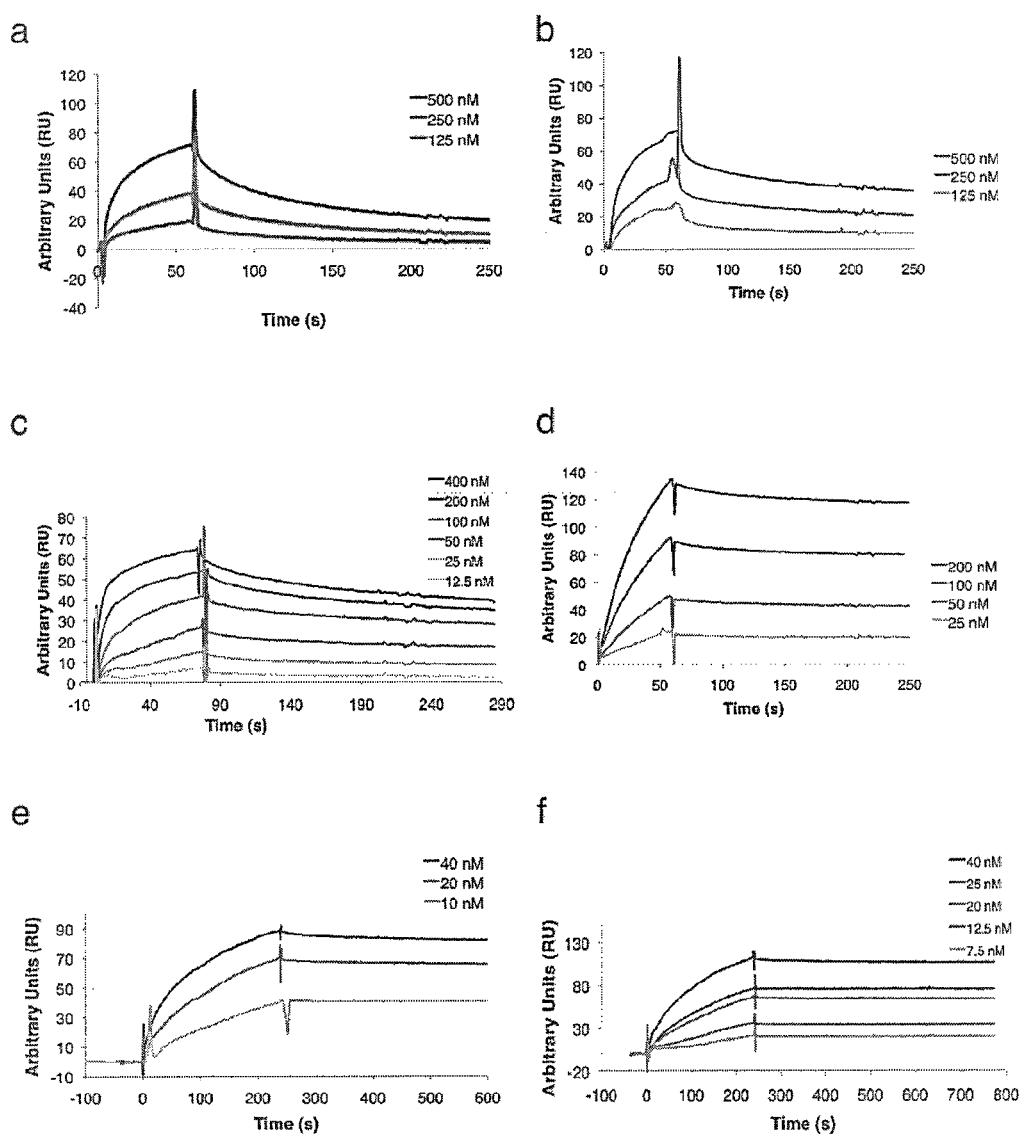
FIG. 3 depicts BIAcore sensograms of IL-17A-binding polypeptides of the invention: (a) Clone B1_2 (SEQ ID NO: 39), (b) E4 (SEQ ID NO: 57), (c) 2C1 (SEQ ID NO: 107), (d) E4-Fc (SEQ ID NO: 117), (e) 2C1-Fc (SEQ ID NO: 118), f) $(2C1)_2$-Fc (SEQ ID NO: 119).

The binding properties were analyzed by real-time interaction analysis on a BIAcore chip (FIG. 3) revealing the following dissociation constants (K$_D$) for selected IL-17A-binding polypeptides and fusion proteins:

TABLE II

| Clone | SEQ ID NO: | K$_D$ |
|---|---|---|
| B1_2 | 39 | 117 nM |
| E4 | 57 | 31 nM |
| 2C1 | 107 | 5 nM |
| E4-Fc | 117 | 5 nM |

TABLE II-continued

| Clone | SEQ ID NO: | K$_D$ |
|---|---|---|
| 2C1-Fc | 118 | 305 pM |
| [(2C1)$_2$-Fc] | 119 | 180 pM |

Example 3

IL-17A Inhibition Cell Assay

IL-17A induces the production of IL-6 in fibroblasts in a dose-dependent manner (Yao et al. (1995) Immunity, 3, p. 811-821). The inhibitory activities of the indicated Fyn SH3-derived IL-17A-binding polypeptides and fusion proteins were tested by stimulating human dermal fibroblasts with recombinant IL-17A in the absence or presence of various concentrations of Fyn SH3 mutants or human IL-17A receptor-Fc chimera. Cell culture supernatants were taken after 24 h of stimulation and assayed for IL-6 with ELISA. In addition, a colorimetric test was performed using the reagent XTT in order to demonstrate that the cells were viable after 24 h of incubation with IL-17A alone, or IL-17A and Fyn SH3-derived inhibitory IL-17A-binding polypeptides of the invention, or IL-17A and IL-17R-Fc chimera. Only viable and metabolic active cells are capable of reducing the tetrazolium salt XTT to orange-colored compounds of formazan (Scudiero, et al. (1988), Cancer Res. 48, p. 4827-4833).

Methods

For endotoxin removal the indicated protein solutions were filtered three times with the Acrodisc Mustang E membrane. (VWR). After filtration the endotoxin levels of the protein solutions containing inhibitory Fyn SH3-derived IL-17A-binding polypeptides of the invention were less than 0.1 EU/ml, as determined by the *Limulus amebocyte* lysate (LAL) test (PYROGENT Single test Gel Clot LAL Assay (Lonza)).

400 µl of a cell suspension containing about 1×10$^4$ Normal Human Dermal Fibroblasts (PromoCell, NHDF-c, C12300) were distributed per well (24 well plate, Nunc or TPP) and cultured for 24 hours at 37° C. (medium: Fibroblast Growth Medium C-23010, PromoCell). The supernatant was aspirated and after mixing different concentrations of Fyn SH3 derived IL-17A-binding polypeptides of the invention or IL-17A receptor Fc chimera (RnD Systems) with IL-17A (RnD Systems) containing medium (50 ng/ml final concentration), 350 µl of the corresponding solution was added per well (mixing ratio between inhibitor solution and IL-17A-containing medium was 1:3). As a positive control PBS was mixed with the IL-17A containing medium ("no inhibitor") in a ratio of 1:3 and as a negative control PBS was mixed with medium only ("no IL-17A") in a ratio of 1:3. For the determination of the IL-17A-dependent IL-6 production, IL-17A containing medium was used (final concentrations of IL-17A: 10, 25 and 50 ng/ml) and mixed with PBS in a ratio of 3:1. After 24 hours incubation at 37° C. the supernatant was aspirated and the IL-6 concentration was determined by ELISA according to the manufacturer's instructions (IL-6 ELISA kit, R&D Systems). Immediately after the aspiration of the supernatant the XTT-containing medium was added (Cell Proliferation Kit II, Roche) and cell viability was determined according to the manufacturer's instructions.

The percentage of IL-17A inhibition was determined with the following formula:

Inhibition (%) =

$$100 - \frac{(A450\text{-}650 \text{ nm (sample)} - A450\text{-}650 \text{ nm (neg. control)}) \times 100}{(A450\text{-}650 \text{ nm (pos. control)} - A450\text{-}650 \text{ nm (neg. control)})}$$

Results

Normal Human Dermal Fibroblasts (NHDF) were incubated with IL-17A at different concentrations. FIG. 4 (*a*) shows the IL-17A dose-dependent induction of IL-6. In a next step NHDF cells were incubated with IL-17A (50 ng/ml) and different concentrations of indicated Fyn SH3-derived IL-17A-binding polypeptides of the invention or IL-17A receptor-Fc chimera (FIG. 4(*b*)). It was observed that both clones 2C1 (SEQ ID NOD: 107) and E4 (SEQ ID NO: 57) inhibited the IL-17A induced IL-6 production with $IC_{50}$ values of about 1 nM and 6 nM, respectively. The IL-17A receptor-Fc chimera has a reported $IC_{50}$ value of 500 pM (R&D Systems). In this experiment, a value of about 1 nM was obtained. The assay depicts a representative result of three independent experiments. In order to further demonstrate that the inhibition of IL-6 production was a consequence of a specific IL-17A neutralization, the cells were incubated with the Fyn SH3 wt domain (Grabulovski et al. (2007) JBC, 282, p. 3196-3204) as a protein of irrelevant binding specificity in presence of IL-17A (FIG. 4 (*c*)). As expected, no inhibition of IL-6 production was observed, whereas clone 2C1 (SEQ ID NOD: 107) was capable of inhibiting IL-17A-induced 11-6 production. In FIG. 4(*d*) the XTT assay is shown, confirming that all cells were viable after incubation with Fyn SH3-derived IL-17A-binding polypeptides of the invention (at a concentration of 750 nM) and IL-17 receptor (10 nM) for 24 hours.

Example 4

Stability

A crucial aspect of any biological compound intended for therapeutic applications is its stability and resistance to aggregation when stored in solution. Fyn SH3-derived IL-17A-binding polypeptides of the invention are particularly useful drug and diagnostic candidates because they have proven stable when stored at 4° C. or at −20° C. for at least 6 months in simple phosphate-buffered saline.

Methods

Protein solutions of the IL-17A-binding polypeptides of the invention were stored for 6 months at 4° C. and at −20° C. after purification. In order to analyze protein stability and aggregation state, the protein solutions were filtered (Millex GP, 0.22 μm, Millipore) and size exclusion chromatography (SEC) was performed on an ÄKTA FPLC system using a Superdex 75 Short Column (5/150) (GE Healthcare)

Results

Fyn SH3-derived IL-17A-binding polypeptide G3 (SEQ ID NO: 34) was produced with an expression yield of 123 mg/L and eluted mainly as single peak from the size exclusion chromatography column (see FIG. 5).

The stability and aggregation resistance of G3 (SEQ ID NO: 34) was assessed by storing the protein at 4° C. and −20° C. in PBS. After 6 months the status of the protein was examined by size exclusion chromatography. The measurements did not reveal any sign of aggregation or degradation. The elution profiles after 6 months of storage are shown in FIG. 6.

Example 5

In Vivo Half-Life

The in vivo half-life of the fusion protein of the invention E4-Fc (SEQ ID NO: 117) was determined by measuring E4-Fc (SEQ ID NO: 117) concentrations in mouse serum at different time points after a single i.v. injection by ELISA.

Methods

Cloning and expression of E4-Fc (SEQ ID NO: 117) is described in Example 2. 200 μl of a 3.3 μM (0.22 mg/ml) solution of E4-Fc (SEQ ID NO: 117) was injected i.v. into 5 mice (C57BU6, Charles River). After 7 minutes, 20 minutes, 1, 2, 4, 8, 24 and 48 h about 20 μl of blood were taken from the vena saphena with the capillary Microvette CB 300 (Sarstedt). The blood samples were centrifuged for 10 min at 9500×g and the serum was stored at −20° until ELISA analysis was performed. Using an E4-Fc (SEQ ID NO: 117) dilution series with known concentrations, the E4-Fc (SEQ ID NO: 117) concentration in serum was determined by ELISA: 50 μl of biotinylated IL-17A (30 nM) (R&D Systems, biotinylated using NHS-PEO4-biotin (Pierce) according to the manufacturer's instructions) were added to streptavidin-coated wells (Reactibind, Pierce) and after blocking with PBS, 4% milk (Rapilait, Migros, Switzerland), 45 μl of PBS, 4% milk and 5 μl of serum sample were added. After incubation for 1 h and washing, bound Fc fusion proteins were detected with protein A-HRP conjugate (Sigma). Peroxidase activity was detected by addition of QuantaRed enhanced chemifluorescent HRP substrate (Pierce). Fluorescence intensity was measured after 5 to 10 min at 544 nm (excitation) and 590 nm (emission). From the concentrations of E4-Fc (SEQ ID NO: 117) determined in serum (n 3 per time point, except last time point: n=1) at different time points and the resulting slope k of the elimination phase (plotted in a semi-logarithmic scale) the half-life of E4-Fc (SEQ ID NO: 117) was calculated using to the formula $t^{1/2}=\ln2/-k$.

Results

The half-life of fusion protein of the invention E4-Fc (SEQ ID NO:117) as calculated from the elimination phase (beta phase, 4 last time points) was 50.6 hours (see FIG. 7).

Example 6

Elisa for Determining the Binding Specificity of IL-17A-Binding Polypeptides and Fusion Proteins Methods Target proteins human IL-17F (R&D systems), murine IL-17A (R&D Systems), human TNF-alpha (Thermo Scientific), human IL-6 (R&D Systems), bovine serum albumin (Sigma) and ovalbumin (Sigma) were coated on a MaxiSorp plate (Nunc) overnight (100 μl of each target at a concentration of 5 μg/ml). Wells were washed three times with PBS and after blocking with 200 μl of PBS, 4% Milk (Rapilait, Migros) and a washing step with PBS (as above), 50 μl of 2C1 (SEQ ID No: 107) at a final concentration of 50 nM were added to the wells together with 50 μl of an anti-myc antibody (9E10, produced in-house, a stock solution of OD=2 and diluted 1:250 in PBS, 2% milk). After incubation the wells were washed three times with PBS and 100 μl of anti-mouse-HRP immunoconjugate (Sigma) diluted 1:1000 in PBS, 2% milk were added to the wells. The 96-well plate was incubated for 1 h at RT and then washed three times with PBS, 0.1% Tween followed by three washes with PBS only. Colorimetric detection was done by addition of 100 μl of BM blue POD substrate (Roche) and the reaction was stopped with 60 μl 1 M $H_2SO_4$.

Results

Clone 2C1 (SEQ ID No: 107) bound human IL-17A in a highly specific manner and did not cross-react with any of the other tested proteins as shown by ELISA (FIG. 8). A small signal above background was observed for IL-17F, but when 2C1 was probed to a IL-17F coated BIAcore chip, no detectable binding was determined (data not shown).

Example 7

Fyn SH3-Derived Polypeptide of the Invention Binds Specifically and with High Affinity to Human and Cynomolgus IL-17A

Methods
a) Specificity

For the determination of the binding specificity of IL-17A-binding polypeptides of the invention, the following target proteins were used (more target proteins compared to Example 6):
- human IL-17A (R & D Systems)
- human IL-17B (Peprotech)
- human IL-17C(R & D Systems)
- human IL-17D (Peprotech)
- human IL-17E (Peprotech)
- human IL-17F (Abd Serotec)
- mouse IL-17A (R & D Systems)
- rat IL-17A (Akron Biotech)
- canine IL-17A (R & D Systems)
- cynomolgus (*macaca fascicularis*) IL-17A (produced in-house in *E. coli*, without signal peptide, with a C-terminal glycine residue followed by a hexa-his tag, refolded from inclusion bodies, SEQ ID NO: 129)
- extra domain B of fibronectin (produced in-house, *E. coli*; see Carnemolla et al. (1996) Int J Cancer, 68(3), p. 397-405)
- Human IL-6 (R & D Systems)
- Human TNF alpha (Thermo Scientific)
- Ovalbumin (Sigma)
- BSA (Sigma)

The target proteins were coated on a MaxiSorp plate (Nunc) overnight (100 µl of each target at a concentration of 10 µg/ml). Wells were washed three times with PBS and after blocking with 200 µl of PBS, 4% Milk (Rapilait, Migros) for 1 hour at room temperature and a subsequent washing step with PBS (as above), 50 µl of the Fyn SH3-derived polypeptide of the invention 2C1 (SEQ ID No: 107) at a final concentration of 80 nM were added to the wells together with 50 µl of anti-myc antibody 9E10 (produced in-house, a stock solution of OD=2 and diluted 1:250 in PBS, 2% milk). After incubation the wells were washed three times with PBS and 100 µl of anti-mouse-HRP immunoconjugate (Sigma) diluted 1:1000 in PBS, 2% milk were added to the wells. The 96-well plate was incubated for 1 h at RT and then washed three times with PBS, 0.1% Tween followed by three washes with PBS only. Colorimetric detection was done by addition of 100 µl of BM blue POD substrate (Roche) and the reaction was stopped with 60 µl 1 M $H_2SO_4$.

b) Affinity Measurements To Cynomolgus IL-17A

Affinity measurements were performed using a BIAcore 3000 instrument (Biacore). For the interaction analysis between cynomolgus IL-17A and the Fyn SH3-derived polypeptide of the invention 2C1 (SEQ ID NO: 107) a CM5 chip (Biacore) was coated with 6900 RU cynomolgus IL-17A. The running buffer was HBS-EP (Biacore). The interactions were measured at a flow of 20 µl/min and injection of different concentrations of Fyn SH3-derived IL-17A-binding polypeptide of the invention 2C1 (SEQ ID NO: 107). All kinetic data of the interaction (separate kon/koff) were evaluated using BIA evaluation 3.2RC1 software.

Results

Fyn SH3-derived polypeptide of the invention 2C1 (SEQ ID No: 107) bound human and cynomolgus IL-17A in a highly specific manner and did not cross-react with any of the other tested proteins as shown by ELISA (FIG. 9).

The affinity of monomeric Fyn SH3-derived polypeptide of the invention 2C1 (SEQ ID NO:107) for cynomolgus IL-17A was measured with Biacore using cynomolgus IL-17A produced in *E. coli* (refolded from inclusion bodies). 2C1 was found to bind cynomolgus IL-17A with a $K_D$ of 11 nM (FIG. 10).

Example 8

Expression of Fyn SH3-Derived Polypeptides of the Invention Fused to an Fc Part and to a Modified Fc Part of a Human IgG1 Antibody in Mammalian Cells

The Fyn SH3-derived polypeptide of the invention 2C1 (SEQ ID NO: 107) was genetically fused to the Fc part of IgG1 (2C1-Fc, SEQ ID NO: 130) and expressed in HEK EBNA cells. The Fyn SH3-derived polypeptide of the invention 2C1 (SEQ ID NO: 107) was also cloned as genetic fusion to the modified Fc part of human IgG1, comprising mutations L234A (alanine instead of leucine at amino acid position 234) and L235A and expressed in HEK EBNA cells (2C1-Fc (LALA), SEQ ID NO: 131). Furthermore, the following four variants of 2C1-Fc(LALA) fusion protein with different linker length between the Fyn SH3-derived polypeptide of the invention and the Fc part were produced:
- (SEQ ID NO: 132) "2C1-m5E-Fc(LALA)"; extension of hinge region by 5 amino acids: EPKSS linker
- (SEQ ID NO: 133) "2C1-m5-Fc(LALA)"; 5 amino acids extension, GGGGS linker
- (SEQ ID NO: 134) "2C1-m10-Fc(LALA)"; 10 amino acids extension, $(GGGGS)_2$ linker
- (SEQ ID NO: 135) "2C1-m15-Fc(LALA)"; 15 amino acids extension, $(GGGGS)_3$ linker Methods Cloning of "2C1-Fc": Fyn SH3-Derived Polypeptide of the Invention 2C1 (SEQ ID NO:107) Fused to an Fc Part of a Human IgG1 Antibody (SEQ ID NO: 130)

The gene encoding clone 2C1 (SEQ ID NO: 107) was used as a template and amplified using the primers SB3 (5' CGA ATT CGG GAG TGA CAC TCT TTG TGG CCC 3', SEQ ID NO: 136) and SB4 (5' GAA GAT CTC TGG ATA GAG TCA ACT GGA GCC 3', SEQ ID NO: 137) introducing the restriction sites EcoRI and BglII. Obtained PCR product was digested with EcoRI and BglII and cloned into the previously double-digested pFUSE-hIgG1-Fc2 vector (Invivogen). For cloning this Fc fusion into the pCEP4 vector (Invitrogen), the resulting pFUSE vector containing the gene encoding the 2C1-Fc fusion was used as template and amplified with the primers SB5 (5' CCC AAG CTT GGG ATG GGC TAC AGG ATG CAA CTC CTG TC 3', SEQ ID NO: 138) and SB6 (5' CGG GAT CCT CAT TTA CCC GGA GAO AGG GAG 3', SEQ ID NO: 139), introducing HindIII and BamHI restriction sites. After digestion with HindIII/BamHI, the insert was ligated with previously double-digested pCEP4 vector, yielding the plasmid containing the genetic information of SEQ ID NO: 130.

Cloning of "2C1-Fc(LALA)": Fyn SH3-Derived Polypeptide of the Invention 2C1 (SEQ ID NO:107) Fused to a Modified Fc Part of a Human IgG1 Antibody (L234A, L235A) (Yielding SEQ ID NO: 131)

The above mentioned plasmid containing the genetic information of 2C1-Fc (SEQ ID NO: 130) was used as a template for two PCR reactions. In the first reaction, the primers SB5 and SB7 (5' ACT GAC GGT CCC CCC GCG GCT TCA GGT GCT GGG CAC 3', SEQ ID NO: 140) were used. In the second PCR the primers SB8 (5' GCC GCG GGG GGA CCG TCA GTC TTC CTC TTC CC 3', SEQ ID NO: 141) and SB6 were used. A PCR assembly with both fragments as templates was performed, the resulting PCR product was digested with BamHI and HindIII and ligated with the digested pCEP4 vector as described above.

Cloning of "2C1-m5E-Fc(LALA)" (SEQ ID NO: 132): Fyn SH3-Derived Polypeptide of the Invention 2C1 (SEQ ID NO: 107) Fused with a 5 Amino Acid Linker EPKSS to a Modified Fc Part of a Human IgG1 Antibody (L234A, L235A)

The above mentioned plasmid containing the genetic information of 2C1-Fc(LALA) (SEQ ID NO: 131) was used as a template for two PCRs. In the first reaction the primers SB5 and "Ba_2Cl_R_EPKSS" (5' GCT GCT TTT CGG TTC CTG GAT AGA GTC AAC TGG AGC CAC 3', SEQ ID NO: 142) were used. In the second reaction the primers SB6 and "Ba_Hinge_F_EPKSS" (5' GAA CCG AAA AGC AGC GAC AAA ACT CAC ACA TGC CCA CCG 3', SEQ ID NO: 143) were used. A PCR assembly with both fragments as templates was performed, the resulting PCR product was digested with BarnHI and HindIII and ligated with the digested pCEP4 vector as described above.

Cloning of "2C1-m5-Fc(LALA)" (SEQ ID NO: 133): Fyn SH3-Derived Polypeptide of the Invention 2C1 (SEQ ID NO: 107) Fused with a 5 Amino Acid Linker GGGGS to a Modified Fc Part of a Human IgG1 Antibody (L234A, L235A)

The above mentioned plasmid containing the genetic information of 2C1-Fc(LALA) (SEQ ID NO: 131) was used as a template for two PCRs. In the first reaction the primers SB5 and 47c.fo (5' TGA ACC GCC TCC ACC CTG GAT AGA GTC AAC TGG AGC CAC 3', SEQ ID NO: 144) were used. In the second reaction the primers SB6 and "Ba_Hinge_F_5aaGS-linker" (5' GGT GGA GGC GGT TCA GAC AAA ACT CAC ACA TGC CCA CCG 3', SEQ ID NO: 145) were used. A PCR assembly with both fragments as templates was performed, the resulting PCR product was digested with BamHI and HindIII and ligated with the digested pCEP4 vector as described above.

Cloning of "2C1-m10-Fc(LALA)" (SEQ ID NO: 134): Fyn SH3-Derived Polypeptide of the Invention 2C1 (SEQ ID NO:107) Fused with a 10 Amino Acid Linker (GGGGS)$_2$ to a Modified Fc Part of a Human IgG1 Antibody (L234A, L235A)

The above mentioned plasmid containing the genetic information of 2C1-Fc(LALA) (SEQ ID NO: 131) was used as a template for two PCRs. In the first reaction the primers SB5 and 47b.fo (5' AGA GCC ACC TCC GCC TGA ACC GCC TCC ACC CTG GAT AGA GTC AAC TGG AGC CAC 3', SEQ ID NO: 146) were used. In the second reaction the primers SB6 and "Ba_Hinge_F_10aaGS-linker" (5' GGT GGA GGC GGT TCA GGC GGA GGT GGC TCT GAC AAA ACT CAC ACA TGC CCA CCG 3', SEQ ID NO: 147) were used. A PCR assembly with both fragments as templates was performed, the resulting PCR product was digested with BamHI and HindIII and ligated with the digested pCEP4 vector as described above.

Cloning of "2C1-m15-Fc(LALA)" (SEQ ID NO: 135): Fyn SH3-Derived Polypeptide of the Invention 2C1 (SEQ ID NO:107) Fused with a 15 Amino Acid Linker (GGGGS)$_3$ to a Modified Fc Part of a Human IgG1 Antibody (L234A, L235A)

The above mentioned plasmid containing the genetic information of 2C1-Fc(LALA) (SEQ ID NO: 131) was used as a template for two PCRs. In the first reaction the primers SB5 and 47.fo.corr (5' TGA TCC GCC ACC GCC AGA GCC ACC TCC GCC TGA ACC GCC TCC ACC CTG GAT AGA GTC AAC TGG AGC CAC 3', SEQ ID NO: 148) were used. In the second reaction the primers SB6 and "Ba_Hinge_F_15aaGS-linker" (5' GGT GGA GGC GGT TCA GGC GGA GGT GGC TCT GGC GGT GGC GGA TCA GAC AAA ACT CAC ACA TGC CCA CCG 3', SEQ ID NO: 149) were used. A PCR assembly with both fragments as templates was performed, the resulting PCR product was digested with BamHI and HindIII and ligated with the digested pCEP4 vector as described above.

For expression of the fusion proteins, the corresponding plasmids were purified using an endotoxin free Megaprep kit (Qiagen) and used for transient transfection of HEK EBNA cells (ATCC No CRL-10852). HEK EBNA cells were seeded at 30% confluence 24 hours prior to transfection. The medium was replaced with DMEM/5% FCS/penstrep (Invitrogen) immediately prior to transfection. 60 µg of DNA was used to transfect 150 cm$^2$ of adherent cells. DNA and PEI (25 kDa from Polysciences) were mixed in a 1:3 ratio and vortexed for 10 sec. Then, the DNA/PEI mixture was incubated at RT for 10 minutes and subsequently added to the HEK EBNA cells. After 24 hours the medium was replaced with CD-CHO/HT/L-glutamine/Penstrep (Invitrogen) and incubated at 37° C. with 5% $CO_2$. The cell culture supernatant was harvested after 96 hours.

For protein purification, the cell culture supernatant was applied to a protein A-sepharose affinity column. Subsequently, the column was washed with PBS followed by protein elution using 0.1 M glycine pH 2.7. Eluted protein was then dialysed into PBS. If needed, a second purification step for removal of endotoxins with Triton-X114 was performed (Magalhaes et al. (2007) J Pharm Pharmaceut Sci, 10(3), p. 388-404).

Results

The Fyn SH3-derived Fc fusions of the invention could be expressed and purified. FIG. 11 shows the SDS PAGE analysis of the Fc fusion proteins.

Example 9

Fyn SH3-Derived Polypeptides of the Invention are Stable in Human Serum

Protein drugs should be stable in serum for a certain period of time, in order to be able to elicit pharmacodynamic effects in patients. In this example, the serum stability of 2C1-Fc (SEQ ID NO: 130) was tested.

Methods

A solution of 3 ml of human serum (Sigma) containing 10 µg/ml 2C1-Fc (SEQ ID NO: 130) was prepared and placed in an incubator at 37° C. 200 µl samples were removed at indicated time points and frozen at −20° C. until the end of the experiment. After 5 days, an ELISA was performed with the collected samples, using a 2C1-Fc sample (SEQ ID NO: 130) which has been stored at 4° C. in PBS as a control standard.

To perform the ELISA, IL-17A (R&D Systems) was coated on a MaxiSorp plate (Nunc) overnight (100 µl of 5 µg/ml). Wells were washed three times with PBS and after blocking with 200 µl of PBS, 4% Milk (Rapilait, Migros) and a washing step with PBS (as above), 1000 of the test samples comprising 2C1-Fc (SEQ ID NO: 130) (at the indicated concentrations) diluted in PBS, 2% Milk were added. After incubation, the wells were washed three times with PBS, followed by addition of 100 µl Protein A-HRP (Sigma) diluted 1:1000 in PBS, 2% milk. The 96-well plate was incubated for 1 h at RT and then washed three times with PBS, 0.1% Tween followed by three washes with PBS only. Colorimetric detection was done by addition of 100 µl of BM blue POD substrate (Roche) and the reaction was stopped with 60 µl 1 M $H_2SO_4$.

Results

After a 5-day storage period in human serum at 37° C. 2C1-Fc (SEQ ID NO: 130) was able to bind its target IL-17A essentially as well as 2C1-Fc (SEQ ID NO: 130) which was stored in PBS at 4° C., indicating that 2C1-Fc (SEQ ID NO: 130) is stable in human serum at 37° C. (FIG. 12).

Example 10

Fyn SH3-Derived Polypeptides of the Invention Inhibit IL-17A In vitro

In this assay the indicated Fyn SH3-derived polypeptides of the invention were tested for their ability to inhibit IL-17A in vitro. The cell assay is similar to the cell assay described in Example 3 of this invention, with the main exception that IL-17A is used at a low concentration of 1 ng/ml (compared to 50 ng/ml in Example 3) together with TNF alpha (50 µg/ml).

Methods

Endotoxin levels of tested Fyn SH3-derived IL-17A-binding polypeptides of the invention were less than 0.1 EU/ml, as determined by the *Limulus amebocyte* lysate (LAL) test (PYROGENT Single test Gel Clot LAL Assay (Lonza)).

Normal human dermal fibroblasts (NHDF, PromoCell Inc., NHDF-c, C12300) are used for the IL-17A inhibition cell assay. Addition of human IL-17A (R&D Systems) in combination with human tumor necrosis factor-α (TNF-α, Thermo Fisher Scientific) to the cell culture medium induces IL-6 production by NHDF cells in a dose-dependent manner. IL-6 released into the cell culture medium (PromoCell, C-23010) is quantified in cell culture supernatant by ELISA using a commercially available ELISA kit (R&D Systems, DuoSet ELISA System kit (DY206)).

$10^4$ Normal Human Dermal Fibroblasts (PromoCell, NHDF-c, C12300) were distributed per well (24 well plate, Nunc or TPP) and cultured for 24 hours at 37° C. (medium: Fibroblast Growth Medium C-23010, PromoCell). The supernatant was aspirated and after mixing different concentrations of Fyn SH3 derived IL-17A-binding polypeptides of the invention or IL-17A receptor Fc chimera (RnD Systems) with IL-17A (RnD Systems) and TNF alpha (Thermo Scientific) containing medium (1 ng/ml final IL-17A concentration and 50 µg/ml TNF alpha), 350 µl of the corresponding solution was added per well, in triplicate (mixing ratio between inhibitor solution and cytokine-containing medium was 1:23). Control wells included incubation without Fyn SH3-derived polypeptides (PBS only), IL-17A alone, TNF-α alone and medium only. After 24 hours incubation at 37° C. the supernatant was aspirated and the ELISA absorbance (correlating to the IL-6 concentration) was determined by ELISA according to the manufacturer's instructions (IL-6 ELISA kit, R&D Systems).

Results

NHDF cells were incubated with a constant concentration of IL-17A (1 ng/ml) and TNF alpha (50 µg/ml) and with different concentrations of the commercially available IL-17A receptor-Fc chimera or with different concentrations of the following Fyn SH3-derived polypeptides of the invention:

2C1 (SEQ ID NO: 107)
2C1-Fc (SEQ ID NO:130)
2C1-Fc(LALA) (SEQ ID NO: 131)
2C1-m5E-Fc(LALA) (SEQ ID NO: 132)
2C1-m5-Fc(LALA) (SEQ ID NO: 133)
2C1-m10-Fc(LALA) (SEQ ID NO: 134)
2C1-m15-Fc(LALA) (SEQ ID NO: 135)

Table III shows the average of the $IC_{50}$ values obtained from several cell assays performed with the indicated Fyn SH3-derived polypeptides of the invention. The best $IC_{50}$ value (0.11 nM) was obtained with 2C1-m15-Fc(LALA) (SEQ ID NO: 135).

TABLE III

Average $IC_{50}$ values of Fyn SH3-derived polypeptides of the invention obtained from several cell assays.

| | $IC_{50}$ value (nM) | Standard Deviation | Number of cell assays |
|---|---|---|---|
| 2C1 (SEQ ID NO: 107) | 2.31 | 0.08 | 3 |
| 2C1-Fc (SEQ ID NO: 130) | 1.13 | 0.30 | 4 |
| 2C1-Fc(LALA) (SEQ ID NO: 131) | 1.09 | 0.53 | 4 |
| 2C1-m5E-Fc(LALA) (SEQ ID NO: 132) | 0.72 | 0.30 | 4 |
| 2C1-m5-Fc (LALA) (SEQ ID NO: 133) | 1.45 | n.d. | 2 |
| 2C1-m10-Fc (LALA) (SEQ ID NO: 134) | 0.27 | 0.13 | 6 |
| 2C1-m15-Fc (LALA) (SEQ ID NO: 135) | 0.11 | 0.02 | 3 |
| IL-17A-Receptor Fc chimera (R&D Systems) | 0.61 | 0.38 | 6 |

Example 11

In Vivo Half-Life of 2C1-Fc(LALA) (SEQ ID NO: 131)

The in vivo half-life of the fusion protein of the invention 2C1-Fc(LALA) (SEQ ID NO: 131) was determined by measuring 2C1-Fc(LALA) (SEQ ID NO: 131) concentrations in mouse serum at different time points after a single i.v. injection.

Methods

2C1-Fc(LALA) (SEQ ID NO: 131) solution (0.2 mg/ml) was injected i.v. into 5 mice (C57BL/6, Charles River), 200 µl per mouse. After indicated time-points about 20 µl of blood were taken from the vena saphena with the capillary Microvette CB 300 (Sarstedt). The blood samples were centrifuged for 10 min at 9500×g and the serum was stored at −20° until ELISA analysis was performed. Using a 2C1-Fc (LALA) (SEQ ID NO: 131) dilution series with known concentrations, the 2C1-Fc(LALA) (SEQ ID NO: 131) concentration in serum was determined by ELISA: 50 µl of biotinylated IL-17A (30 nM) (R&D Systems, biotinylated using NHS-PEO4-biotin (Pierce) according to the manufacturer's instructions) were added to streptavidin-coated wells (Reactibind, Pierce) and after blocking with PBS, 4% milk (Rapilait, Migros, Switzerland), 45 µl of PBS, 4% milk and 5 µl of serum sample were added. After incubation for 1 h and washing, bound Fc fusion proteins were detected with protein A-HRP conjugate (Sigma). Peroxidase activity was detected by addition of QuantaRed enhanced chemifluorescent HRP substrate (Pierce). Fluorescence intensity was measured after 5 to 10 min at 544 nm (excitation) and 590 nm (emission). From the concentrations of 2C1-Fc(LALA) (SEQ ID NO: 131) determined in serum (mouse number n=5 per time point) at different time points and the resulting slope k of the elimination phase (plotted in a semi-logarithmic scale) the half-life of 2C1-Fc(LALA) (SEQ ID NO: 131) was calculated using to the formula $t^{1/2}=\ln2/-k$.

Results

The half-life of fusion protein of the invention 2C1-Fc (LALA) (SEQ ID NO: 131) as calculated from the elimination phase (beta phase, 4 last time points) was 53 hours (see FIG. 13).

Example 12

Fyn SH3-Derived Polypeptides of the Invention Neutralize Human IL-17A In vivo

Human IL-17A is able to bind and stimulate the mouse IL-17 receptor, leading to an elevation and subsequent secretion of mouse KC(CXCL1) chemokine (Allan B. et al. (2007) WO2007/070750 of Eli Lilly, US). The observed KC levels 2 hours after s.c. IL-17A injection (3 μg) were between 500 and 1000 μg/ml in the serum, compared to around 100 μg/ml KC basal levels.

Methods a) In vivo neutralization of IL-17A using monomeric Fyn SH3 derived polypeptide of the invention 2C1 (SEQ ID NO: 107)

Fyn SH3-derived polypeptide of the invention 2C1 (SEQ ID NO: 107) (17 μg) was co-injected (s.c.) with 3 μg of human IL-17A (R&D Systems) into C57BL/6 mice, and 2 hours after injection, blood samples were taken from the vena saphena with the capillary Microvette CB 300 (Sarstedt). The blood samples were centrifuged for 10 min at 9500×g and the serum was stored at −20° until ELISA analysis was performed. KC levels in serum were determined using the commercially available Quantikine mouse CLCL1/KC kit (R&D Systems). Control groups included mice injected with IL-17A and the Fyn SH3 wt domain (see Grabulovski et al. (2007) JBC, 282, p. 3196-3204) as a protein of irrelevant binding specificity, PBS only, IL-17A only, only Fyn SH3-derived polypeptide of the invention 2C1 (SEQ ID NO: 107) or mice given Fyn SH3 wt protein only.

b) In vivo neutralization using the 2C1-Fc fusion (SEQ ID NO: 130):

Fyn SH3-derived polypeptide of the invention 2C1-Fc (SEQ ID NO: 130) (44n/mouse) was injected i.v. into C57BU6 mice. After 20-60 minutes, 3 μg/mouse of human IL-17A (R&D Systems) was injected s.c. and 2 hours after IL-17A injection, blood samples were taken from the vena saphena with the capillary Microvette CB 300 (Sarstedt). The blood samples were centrifuged for 10 min at 9500×g and the serum was stored at −20° until ELISA analysis was performed. KC levels in serum were determined using the commercially available Quantikine mouse CLCL1/KC kit (R&D Systems). Control groups included mice injected with PBS (i.v.) and IL-17A (s.c.), PBS only (i.v. and s.c.), and Fyn SH3-derived polypeptide of the invention 2C1-Fc (SEQ ID NO: 130) i.v. followed by PBS (s.c.).

Results

After s.c. injection of human IL-17A into mice the animals overexpress a chemokine called KC. Elevated KC levels in the sera of mice can be measured by ELISA. Injection of a Fyn SH3-derived polypeptide of the invention prevented the up-regulation of KC.

a)

IL-17A and monomeric Fyn SH3-derived polypeptide 2C1 (SEQ ID NO: 107) of the invention were co-injected s.c. into mice (C57BL/6). Because of the inhibitory properties of the Fyn SH3-derived polypeptide of the invention 2C1 (SEQ ID NO: 107), KC levels were not elevated in this group, they remained low, almost comparable to basal levels. In order to demonstrate that inhibition of KC production was due to specific IL-17A neutralization, mice were co-injected with IL-17A and the wild-type Fyn SH3 domain (which has no binding affinity to IL-17A); in these mice, KC levels were as high as in the group receiving IL-17A only. FIG. 14 shows the results obtained from this experiment.

b)

In this second acute inflammation experiment, the Fyn SH3-derived polypeptide of the invention 2C1-Fc (SEQ ID NO: 130) was injected i.v., followed by s.c. injection of IL-17A. As above in a), the Fyn SH3-derived polypeptide of the invention prevented the up-regulation of KC levels in the serum. FIG. 15 shows the inhibition of IL-17A by 2C1-Fc (SEQ ID NO: 130) in vivo.

The invention claimed is:

1. A polypeptide comprising the amino acid sequence of SEQ ID NO: 39, 57, or 107,
   wherein said polypeptide specifically binds to IL-17A.

2. The polypeptide of claim 1, wherein the polypeptide comprises the amino acid sequence of SEQ ID NO: 39.

3. The polypeptide of claim 1, wherein the polypeptide comprises the amino acid sequence of SEQ ID NO: 57.

4. The polypeptide of claim 1, wherein the polypeptide comprises the amino acid sequence of SEQ ID NO: 107.

5. The polypeptide of claim 1, further comprising a component modulating serum half-life of the polypeptide.

6. The polypeptide of claim 5, wherein said component modulating serum half-life is polyethylene glycol (PEG), immunoglobulin, or an albumin-binding peptide.

7. A polypeptide comprising multimers of the polypeptide of claim 1.

8. A pharmaceutical composition comprising the polypeptide of claim 1.

9. A method for treating an IL-17A- and Th17-mediated disease or medical condition.

10. A fusion protein comprising the polypeptide of claim 1 fused to a pharmaceutically and/or diagnostically active component.

11. The fusion protein according to claim 10, wherein said component is
    (a) a cytokine,
    (b) a toxic compound,
    (c) is a chemokine,
    (d) a fluorescent dye,
    (e) a photosensitizer,
    (f) a pro-coagulant factor,
    (g) an enzyme for prodrug activation,
    (h) a radionuclide, or
    (i) a functional Fc domain.

12. The fusion protein of claim 10, further comprising a component modulating serum half-life of the fusion protein.

13. The fusion protein of claim 12, wherein said component modulating serum half-life is polyethylene glycol (PEG), immunoglobulin, or an albumin-binding peptide.

14. A polypeptide comprising multimers of the fusion protein of claim 10.

15. A method for treating an IL-17A- and Th17-mediated disease or medical condition comprising administering the fusion protein of claim 10.

* * * * *

SEQUENCE LISTING

<160> NUMBER OF SEQ ID NOS: 149

<210> SEQ ID NO 1
<211> LENGTH: 65
<212> TYPE: PRT
<213> ORGANISM: Artificial Sequence
<220> FEATURE:
<223> OTHER INFORMATION: IL-17A binder F2

<400> SEQUENCE: 1

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Gln Gln
            20                  25                  30

Asn Glu Leu Thr Gly Asp Trp Trp Glu Ala Arg Ser Leu Thr Thr Gly
        35                  40                  45

```
Glu Thr Gly Tyr Ile Pro Ser Asn Tyr Val Ala Pro Val Asp Ser Ile
        50                  55                  60

Gln
65

<210> SEQ ID NO 2
<211> LENGTH: 65
<212> TYPE: PRT
<213> ORGANISM: Artificial Sequence
<220> FEATURE:
<223> OTHER INFORMATION: IL-17A binder B3_1

<400> SEQUENCE: 2

Gly Val Thr Leu Phe Val Ala Leu Tyr Asp Tyr Ala Ala Phe Trp Pro
1               5                   10                  15

Gly Asp Leu Ser Phe His Lys Gly Glu Lys Phe Gln Ile Leu Lys Asn
            20                  25                  30

Arg Ala Ile Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 3
<211> LENGTH: 65
<212> TYPE: PRT
<213> ORGANISM: Artificial Sequence
<220> FEATURE:
<223> OTHER INFORMATION: IL-17A binder C2_1

<400> SEQUENCE: 3

Gly Val Thr Leu Phe Val Ala Leu Tyr Asp Tyr Leu Thr Arg Trp Lys
1               5                   10                  15

Pro Asp Leu Ser Phe His Lys Gly Glu Lys Phe Gln Ile Leu Arg Lys
            20                  25                  30

Ile Phe Asp Tyr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 4
<211> LENGTH: 65
<212> TYPE: PRT
<213> ORGANISM: Artificial Sequence
<220> FEATURE:
<223> OTHER INFORMATION: IL-17A binder A2

<400> SEQUENCE: 4

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Tyr Gln
            20                  25                  30

Pro His Ala Leu Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
```

<210> SEQ ID NO 5
<211> LENGTH: 65
<212> TYPE: PRT
<213> ORGANISM: Artificial Sequence
<220> FEATURE:
<223> OTHER INFORMATION: IL-17A binder A5_1

<400> SEQUENCE: 5

```
Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Ser Pro
            20                  25                  30
His Leu Met Phe Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65
```

<210> SEQ ID NO 6
<211> LENGTH: 65
<212> TYPE: PRT
<213> ORGANISM: Artificial Sequence
<220> FEATURE:
<223> OTHER INFORMATION: IL-17A binder D2_1

<400> SEQUENCE: 6

```
Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Asp Thr
            20                  25                  30
Leu Pro Gly Asp Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65
```

<210> SEQ ID NO 7
<211> LENGTH: 65
<212> TYPE: PRT
<213> ORGANISM: Artificial Sequence
<220> FEATURE:
<223> OTHER INFORMATION: IL-17A binder E1_1

<400> SEQUENCE: 7

```
Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Trp Asp
            20                  25                  30
Asp Arg Pro Ala Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65
```

<210> SEQ ID NO 8

```
<211> LENGTH: 65
<212> TYPE: PRT
<213> ORGANISM: Artificial Sequence
<220> FEATURE:
<223> OTHER INFORMATION: IL-17A binder G2_1

<400> SEQUENCE: 8

Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Thr Ser
            20                  25                  30
Asp Leu Arg Met Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65

<210> SEQ ID NO 9
<211> LENGTH: 65
<212> TYPE: PRT
<213> ORGANISM: Artificial Sequence
<220> FEATURE:
<223> OTHER INFORMATION: IL-17A binder G4_1

<400> SEQUENCE: 9

Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Pro Asp
            20                  25                  30
Gln Leu Pro Pro Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65

<210> SEQ ID NO 10
<211> LENGTH: 65
<212> TYPE: PRT
<213> ORGANISM: Artificial Sequence
<220> FEATURE:
<223> OTHER INFORMATION: IL-17A binder H5

<400> SEQUENCE: 10

Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Phe Ser
            20                  25                  30
Ser Tyr Thr Gln Gly Asp Trp Trp Glu Ala Arg Ser Leu Thr Thr Gly
        35                  40                  45
Glu Thr Gly Tyr Ile Pro Ser Asn Tyr Val Ala Pro Val Asp Ser Ile
    50                  55                  60
Gln
65

<210> SEQ ID NO 11
<211> LENGTH: 65
<212> TYPE: PRT
<213> ORGANISM: Artificial Sequence
<220> FEATURE:
```

<223> OTHER INFORMATION: IL-17A binder B1_1

<400> SEQUENCE: 11

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Ala
                20                  25                  30

Ala Glu Pro Phe Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65

<210> SEQ ID NO 12
<211> LENGTH: 65
<212> TYPE: PRT
<213> ORGANISM: Artificial Sequence
<220> FEATURE:
<223> OTHER INFORMATION: IL-17A binder B6

<400> SEQUENCE: 12

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Asn Met
                20                  25                  30

Pro Gln Asp Gly Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65

<210> SEQ ID NO 13
<211> LENGTH: 65
<212> TYPE: PRT
<213> ORGANISM: Artificial Sequence
<220> FEATURE:
<223> OTHER INFORMATION: IL-17A binder E6_1

<400> SEQUENCE: 13

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Glu Ser
                20                  25                  30

Asp Arg Asn Gly Gly Asp Trp Trp Glu Ala Arg Ser Leu Thr Thr Gly
            35                  40                  45

Glu Thr Gly Tyr Ile Pro Ser Asn Tyr Val Ala Pro Val Asp Ser Ile
    50                  55                  60

Gln
65

<210> SEQ ID NO 14
<211> LENGTH: 65
<212> TYPE: PRT
<213> ORGANISM: Artificial Sequence
<220> FEATURE:
<223> OTHER INFORMATION: IL-17A binder A7_1

<400> SEQUENCE: 14

```
Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Asp
            20                  25                  30

Thr Asp Arg Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 15
<211> LENGTH: 65
<212> TYPE: PRT
<213> ORGANISM: Artificial Sequence
<220> FEATURE:
<223> OTHER INFORMATION: IL-17A binder C1_1

<400> SEQUENCE: 15

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu His Ser
            20                  25                  30

Pro Thr Gln Pro Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 16
<211> LENGTH: 65
<212> TYPE: PRT
<213> ORGANISM: Artificial Sequence
<220> FEATURE:
<223> OTHER INFORMATION: IL-17A binder C4_1

<400> SEQUENCE: 16

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Ile
            20                  25                  30

Pro Asn Asp Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 17
<211> LENGTH: 65
<212> TYPE: PRT
<213> ORGANISM: Artificial Sequence
<220> FEATURE:
<223> OTHER INFORMATION: IL-17A binder E2_1

<400> SEQUENCE: 17

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Pro Phe
```

```
                    20                  25                  30

Gln Asp Ser Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 18
<211> LENGTH: 65
<212> TYPE: PRT
<213> ORGANISM: Artificial Sequence
<220> FEATURE:
<223> OTHER INFORMATION: IL-17A binder E5

<400> SEQUENCE: 18

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Pro
            20                  25                  30

Gln Leu Pro Val Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 19
<211> LENGTH: 65
<212> TYPE: PRT
<213> ORGANISM: Artificial Sequence
<220> FEATURE:
<223> OTHER INFORMATION: IL-17A binder E7

<400> SEQUENCE: 19

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Ala
            20                  25                  30

His Gln Leu Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 20
<211> LENGTH: 65
<212> TYPE: PRT
<213> ORGANISM: Artificial Sequence
<220> FEATURE:
<223> OTHER INFORMATION: IL-17A binder H4

<400> SEQUENCE: 20

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser His
            20                  25                  30

Asp Gln Met Phe Gly Asp Trp Trp Glu Ala Arg Ser Leu Thr Thr Gly
        35                  40                  45
```

Glu Thr Gly Tyr Ile Pro Ser Asn Tyr Val Ala Pro Val Asp Ser Ile
    50                  55                  60

Gln
65

<210> SEQ ID NO 21
<211> LENGTH: 65
<212> TYPE: PRT
<213> ORGANISM: Artificial Sequence
<220> FEATURE:
<223> OTHER INFORMATION: IL-17A binder F1_1

<400> SEQUENCE: 21

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu His Trp
            20                  25                  30

Gly Gly His Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 22
<211> LENGTH: 65
<212> TYPE: PRT
<213> ORGANISM: Artificial Sequence
<220> FEATURE:
<223> OTHER INFORMATION: IL-17A binder B3_2

<400> SEQUENCE: 22

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu His Thr
            20                  25                  30

Leu Pro Thr Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 23
<211> LENGTH: 65
<212> TYPE: PRT
<213> ORGANISM: Artificial Sequence
<220> FEATURE:
<223> OTHER INFORMATION: IL-17A binder B4_1

<400> SEQUENCE: 23

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Ser Gly
            20                  25                  30

Pro Gln Tyr Ala Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 24
<211> LENGTH: 65
<212> TYPE: PRT
<213> ORGANISM: Artificial Sequence
<220> FEATURE:
<223> OTHER INFORMATION: IL-17A binder C2_2

<400> SEQUENCE: 24

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Pro His
            20                  25                  30

Lys Met Asn Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 25
<211> LENGTH: 65
<212> TYPE: PRT
<213> ORGANISM: Artificial Sequence
<220> FEATURE:
<223> OTHER INFORMATION: IL-17A binder D2_2

<400> SEQUENCE: 25

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Arg Pro
            20                  25                  30

Thr Ile Pro Pro Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 26
<211> LENGTH: 65
<212> TYPE: PRT
<213> ORGANISM: Artificial Sequence
<220> FEATURE:
<223> OTHER INFORMATION: IL-17A binder D3_1

<400> SEQUENCE: 26

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Val Ser
            20                  25                  30

Asn Gln Thr Thr Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

```
<210> SEQ ID NO 27
<211> LENGTH: 65
<212> TYPE: PRT
<213> ORGANISM: Artificial Sequence
<220> FEATURE:
<223> OTHER INFORMATION: IL-17A binder G4_2

<400> SEQUENCE: 27

Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 28
<211> LENGTH: 65
<212> TYPE: PRT
<213> ORGANISM: Artificial Sequence
<220> FEATURE:
<223> OTHER INFORMATION: IL-17A binder B2_1

<400> SEQUENCE: 28

Gly Val Th

<220> FEATURE:
<223> OTHER INFORMATION: IL-17A binder B5_1

<400> SEQUENCE: 30

Gly Val Thr Leu Phe Val Ala Leu Tyr Asp Tyr Gln Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 31
<211> LENGTH: 65
<212> TYPE: PRT
<213> ORGANISM: Artificial Sequence
<220> FEATURE:
<223> OTHER INFORMATION: IL-17A binder B8

<400> SEQUENCE: 31

Gly Val Thr Leu Phe Val Ala Leu Tyr Asp Tyr Ser Ala Phe Trp Pro
1               5                   10                  15

Gly Asp Leu Ser Phe His Lys Gly Glu Lys Phe Gln Ile Leu Thr Val
            20                  25                  30

Pro Pro Met Gly Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 32
<211> LENGTH: 65
<212> TYPE: PRT
<213> ORGANISM: Artificial Sequence
<220> FEATURE:
<223> OTHER INFORMATION: IL-17A binder C4_2

<400> SEQUENCE: 32

Glu Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Pro His
            20                  25                  30

Lys Met Asn Asp Gly Asp Trp Trp Glu Ala Arg Ser Leu Thr Thr Gly
        35                  40                  45

Glu Thr Gly Tyr Ile Pro Ser Asn Tyr Val Ala Pro Val Asp Ser Ile
    50                  55                  60

Gln
65

<210> SEQ ID NO 33
<211> LENGTH: 65
<212> TYPE: PRT
<213> ORGANISM: Artificial Sequence
<220> FEATURE:
<223> OTHER INFORMATION: IL-17A binder F3_1

<400> SEQUENCE: 33

-continued

Gly Val Thr Leu Phe Val Ala Leu Tyr Asp Tyr Val Ala Phe Trp Pro
1               5                   10                  15
Gly Asp Leu Ser Phe His Lys Gly Glu Lys Phe Gln Ile Leu Thr Val
                20                  25                  30
Pro Pro Met Gly Gly Asp Trp Trp Glu Ala Arg Ser Leu Thr Thr Gly
            35                  40                  45
Glu Thr Gly Tyr Ile Pro Ser Asn Tyr Val Ala Pro Val Asp Ser Ile
        50                  55                  60
Gln
65

<210> SEQ ID NO 34
<211> LENGTH: 65
<212> TYPE: PRT
<213> ORGANISM: Artificial Sequence
<220> FEATURE:
<223> OTHER INFORMATION: IL-17A binder G3

<400> SEQUENCE: 34

Gly Val Thr Leu Phe Val Ala Leu Tyr Asp Tyr Lys Ala Phe Trp Pro
1               5                   10                  15
Gly Asp Leu Ser Phe His Lys Gly Glu Lys Phe Gln Ile Leu His Thr
                20                  25                  30
Leu Pro Thr Asp Gly Asp Trp Trp Glu Ala Arg Ser Leu Thr Thr Gly
            35                  40                  45
Glu Thr Gly Tyr Ile Pro Ser Asn Tyr Val Ala Pro Val Asp Ser Ile
        50                  55                  60
Gln
65

<210> SEQ ID NO 35
<211> LENGTH: 63
<212> TYPE: PRT
<213> ORGANISM: Artificial Sequence
<220> FEATURE:
<223> OTHER INFORMATION: IL-17A binder D3_2

<400> SEQUENCE: 35

Gly Val Thr Leu Phe Val Ala Leu Tyr Asp Tyr Trp Ser Pro Trp Pro
1               5                   10                  15
Ala Asp Leu Ser Phe His Lys Gly Glu Lys Phe Gln Ile Leu Asn Ser
                20                  25                  30
Ser Glu Gly Asp Trp Trp Glu Ala Arg Ser Leu Thr Thr Gly Glu Thr
            35                  40                  45
Gly Tyr Ile Pro Ser Asn Tyr Val Ala Pro Val Asp Ser Ile Gln
        50                  55                  60

<210> SEQ ID NO 36
<211> LENGTH: 63
<212> TYPE: PRT
<213> ORGANISM: Artificial Sequence
<220> FEATURE:
<223> OTHER INFORMATION: IL-17A binder D5

<400> SEQUENCE: 36

Gly Val Thr Leu Phe Val Ala Leu Tyr Asp Tyr His Ser Pro Phe Thr
1               5                   10                  15
Phe Asp Leu Ser Phe His Lys Gly Glu Lys Phe Gln Ile Leu Asn Ser
                20                  25                  30

```
Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 37
<211> LENGTH: 63
<212> TYPE: PRT
<213> ORGANISM: Artificial Sequence
<220> FEATURE:
<223> OTHER INFORMATION: IL-17A binder D2_3

<400> SEQUENCE: 37

```
Gly Val Thr Leu Phe Val Ala Leu Tyr Asp Tyr Gln Ala Phe Trp Pro
1               5                   10                  15

Glu Asp Leu Ser Phe His Lys Gly Glu Lys Phe Gln Ile Leu Asn Ser
            20                  25                  30

Ser Glu Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 38
<211> LENGTH: 63
<212> TYPE: PRT
<213> ORGANISM: Artificial Sequence
<220> FEATURE:
<223> OTHER INFORMATION: IL-17A binder A3_1

<400> SEQUENCE: 38

```
Gly Val Thr Leu Phe Val Ala Leu Tyr Asp Tyr Gln Ala Phe Trp Pro
1               5                   10                  15

Gly Asp Leu Ser Phe His Lys Gly Glu Lys Phe Gln Ile Leu Gln Pro
            20                  25                  30

His Pro Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 39
<211> LENGTH: 63
<212> TYPE: PRT
<213> ORGANISM: Artificial Sequence
<220> FEATURE:
<223> OTHER INFORMATION: IL-17A binder B1_2

<400> SEQUENCE: 39

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 40
<211> LENGTH: 63
<212> TYPE: PRT
<213> ORGANISM: Artificial Sequence
<220> FEATURE:
<223> OTHER INFORMATION: IL-17A binder D3_3

```
<400> SEQUENCE: 40

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Glu Pro
                20                  25                  30

Thr Pro Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 41
<211> LENGTH: 63
<212> TYPE: PRT
<213> ORGANISM: Artificial Sequence
<220> FEATURE:
<223> OTHER INFORMATION: IL-17A binder E2_2

<400> SEQUENCE: 41

Gly Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Thr Val
                20                  25                  30

Tyr Pro Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 42
<211> LENGTH: 63
<212> TYPE: PRT
<213> ORGANISM: Artificial Sequence
<220> FEATURE:
<223> OTHER INFORMATION: IL-17A binder F4

<400> SEQUENCE: 42

Gly Val Thr Leu Phe Val Ala Leu Tyr Asp Tyr Thr Ala Phe Trp Pro
1               5                   10                  15

Gly Asp Leu Ser Phe His Lys Gly Glu Lys Phe Gln Ile Leu Ser Asp
                20                  25                  30

Phe Pro Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
        50                  55                  60

<210> SEQ ID NO 43
<211> LENGTH: 63
<212> TYPE: PRT
<213> ORGANISM: Artificial Sequence
<220> FEATURE:
<223> OTHER INFORMATION: IL-17A binder A6_1

<400> SEQUENCE: 43

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Thr Pro
                20                  25                  30

Ser Asp Gly Asp Trp Trp Glu Ala Arg Ser Leu Thr Thr Gly Glu Thr
            35                  40                  45

Gly Tyr Ile Pro Ser Asn Tyr Val Ala Pro Val Asp Ser Ile Gln
```

<210> SEQ ID NO 44
<211> LENGTH: 63
<212> TYPE: PRT
<213> ORGANISM: Artificial Sequence
<220> FEATURE:
<223> OTHER INFORMATION: IL-17A binder B10

<400> SEQUENCE: 44

```
Gly Val Thr Leu Phe Val Ala Leu Tyr Asp Tyr Lys Ala Phe Trp Pro
1               5                   10                  15
Gly Asp Leu Ser Phe His Lys Gly Glu Lys Phe Gln Ile Leu Gln Phe
            20                  25                  30
Ser Asp Gly Asp Trp Trp Glu Ala Arg Ser Leu Thr Thr Gly Glu Thr
        35                  40                  45
Gly Tyr Ile Pro Ser Asn Tyr Val Ala Pro Val Asp Ser Ile Gln
    50                  55                  60
```

<210> SEQ ID NO 45
<211> LENGTH: 63
<212> TYPE: PRT
<213> ORGANISM: Artificial Sequence
<220> FEATURE:
<223> OTHER INFORMATION: IL-17A binder B12

<400> SEQUENCE: 45

```
Gly Val Thr Leu Phe Val Ala Leu Tyr Asp Tyr Lys Ala Phe Trp Pro
1               5                   10                  15
Gly Asp Leu Ser Phe His Lys Gly Glu Lys Phe Gln Ile Leu Ala Tyr
            20                  25                  30
Ser Asp Gly Asp Trp Trp Glu Ala Arg Ser Leu Thr Thr Gly Glu Thr
        35                  40                  45
Gly Tyr Ile Pro Ser Asn Tyr Val Ala Pro Val Asp Ser Ile Gln
    50                  55                  60
```

<210> SEQ ID NO 46
<211> LENGTH: 63
<212> TYPE: PRT
<213> ORGANISM: Artificial Sequence
<220> FEATURE:
<223> OTHER INFORMATION: IL-17A binder C5_1

<400> SEQUENCE: 46

```
Gly Val Thr Leu Phe Val Ala Leu Tyr Asp Tyr Lys Ala Phe Trp Pro
1               5                   10                  15
Gly Asp Leu Ser Phe His Lys Gly Glu Lys Phe Gln Ile Leu Tyr Ile
            20                  25                  30
Ser Asp Gly Asp Trp Trp Lys Ala Arg Ser Leu Thr Thr Gly Glu Thr
        35                  40                  45
Gly Tyr Ile Pro Ser Asn Tyr Val Ala Pro Val Asp Ser Ile Gln
    50                  55                  60
```

<210> SEQ ID NO 47
<211> LENGTH: 63
<212> TYPE: PRT
<213> ORGANISM: Artificial Sequence
<220> FEATURE:
<223> OTHER INFORMATION: IL-17A binder D12

<400> SEQUENCE: 47

```
Gly Val Thr Leu Phe Val Ala Leu Tyr Asp Tyr Lys Ala Phe Trp Pro
```

```
                1               5                   10                  15
Gly Asp Leu Ser Phe His Lys Gly Glu Lys Phe Gln Ile Leu Gln Tyr
                20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 48
<211> LENGTH: 63
<212> TYPE: PRT
<213> ORGANISM: Artificial Sequence
<220> FEATURE:
<223> OTHER INFORMATION: IL-17A binder D2_4

<400> SEQUENCE: 48

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Lys Tyr
                20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 49
<211> LENGTH: 63
<212> TYPE: PRT
<213> ORGANISM: Artificial Sequence
<220> FEATURE:
<223> OTHER INFORMATION: IL-17A binder B2_2

<400> SEQUENCE: 49

```
Gly Val Thr Leu Phe Val Ala Leu Tyr Asp Tyr Leu Ala Phe Trp Pro
1               5                   10                  15

Gly Asp Leu Ser Phe His Lys Gly Glu Lys Phe Gln Ile Leu Arg Thr
                20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 50
<211> LENGTH: 63
<212> TYPE: PRT
<213> ORGANISM: Artificial Sequence
<220> FEATURE:
<223> OTHER INFORMATION: IL-17A binder D2_5

<400> SEQUENCE: 50

```
Gly Val Thr Leu Phe Val Ala Leu Tyr Asp Tyr Val Ala Phe Trp Pro
1               5                   10                  15

Gly Asp Leu Ser Phe His Lys Gly Glu Lys Phe Gln Ile Leu Arg Thr
                20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 51

```
<211> LENGTH: 63
<212> TYPE: PRT
<213> ORGANISM: Artificial Sequence
<220> FEATURE:
<223> OTHER INFORMATION: IL-17A binder D7_1

<400> SEQUENCE: 51

Gly Val Thr Leu Phe Val Ala Leu Tyr Asp Tyr Ile Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 52
<211> LENGTH: 63
<212> TYPE: PRT
<213> ORGANISM: Artificial Sequence
<220> FEATURE:
<223> OTHER INFORMATION: IL-17A binder C11

<400> SEQUENCE: 52

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Gln
        35                  40                  45

Gly Tyr Ile Pro Ser Asn Tyr Val Ala Pro Val Asp Ser Ile Gln
    50                  55                  60

<210> SEQ ID NO 53
<211> LENGTH: 63
<212> TYPE: PRT
<213> ORGANISM: Artificial Sequence
<220> FEATURE:
<223> OTHER INFORMATION: IL-17A binder A1_2

<400> SEQUENCE: 53

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60

<210> SEQ ID NO 54
<211> LENGTH: 63
<212> TYPE: PRT
<213> ORGANISM: Artificial Sequence
<220> FEATURE:
<223> OTHER INFORMATION: IL-17A binder B7_1

<400> SEQUENCE: 54

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30
```

-continued

Ser Asp Gly Glu Trp Trp Ile Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60

<210> SEQ ID NO 55
<211> LENGTH: 63
<212> TYPE: PRT
<213> ORGANISM: Artificial Sequence
<220> FEATURE:
<223> OTHER INFORMATION: IL-17A binder B5_2

<400> SEQUENCE: 55

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60

<210> SEQ ID NO 56
<211> LENGTH: 63
<212> TYPE: PRT
<213> ORGANISM: Artificial Sequence
<220> FEATURE:
<223> OTHER INFORMATION: IL-17A binder H11_1

<400> SEQUENCE: 56

Gly Val Thr Leu Phe Val Ala Leu Tyr Asp Tyr Lys Ala Phe Trp Pro
1               5                   10                  15

Gly Asp Val Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60

<210> SEQ ID NO 57
<211> LENGTH: 63
<212> TYPE: PRT
<213> ORGANISM: Artificial Sequence
<220> FEATURE:
<223> OTHER INFORMATION: IL-17A binder E4

<400> SEQUENCE: 57

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 58
<211> LENGTH: 63
<212> TYPE: PRT
<213> ORGANISM: Artificial Sequence
<220> FEATURE:

<223> OTHER INFORMATION: IL-17A binder F3_2

<400> SEQUENCE: 58

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 59
<211> LENGTH: 63
<212> TYPE: PRT
<213> ORGANISM: Artificial Sequence
<220> FEATURE:
<223> OTHER INFORMATION: IL-17A binder A3_2

<400> SEQUENCE: 59

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Met Ala Arg Ser Leu Thr Thr Gly Glu Val
        35                  40                  45

Gly Tyr Ile Pro Ser Asn Tyr Val Ala Pro Val Asp Ser Ile Gln
    50                  55                  60

<210> SEQ ID NO 60
<211> LENGTH: 63
<212> TYPE: PRT
<213> ORGANISM: Artificial Sequence
<220> FEATURE:
<223> OTHER INFORMATION: IL-17A binder A5_2

<400> SEQUENCE: 60

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Val Ala Arg Ser Leu Thr Thr Gly Glu Asp
        35                  40                  45

Gly Tyr Ile Pro Ser Asn Tyr Val Ala Pro Val Asp Ser Ile Gln
    50                  55                  60

<210> SEQ ID NO 61
<211> LENGTH: 63
<212> TYPE: PRT
<213> ORGANISM: Artificial Sequence
<220> FEATURE:
<223> OTHER INFORMATION: IL-17A binder A8

<400> SEQUENCE: 61

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Asp Trp Trp Tyr Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60

<210> SEQ ID NO 62
<211> LENGTH: 63
<212> TYPE: PRT
<213> ORGANISM: Artificial Sequence
<220> FEATURE:
<223> OTHER INFORMATION: IL-17A binder H10

<400> SEQUENCE: 62

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60

<210> SEQ ID NO 63
<211> LENGTH: 63
<212> TYPE: PRT
<213> ORGANISM: Artificial Sequence
<220> FEATURE:
<223> OTHER INFORMATION: IL-17A binder A9

<400> SEQUENCE: 63

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60

<210> SEQ ID NO 64
<211> LENGTH: 63
<212> TYPE: PRT
<213> ORGANISM: Artificial Sequence
<220> FEATURE:
<223> OTHER INFORMATION: IL-17A binder B2_3

<400> SEQUENCE: 64

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Gly Asp
        35                  40                  45

Gly Tyr Ile Pro Ser Asn Tyr Val Ala Pro Val Asp Ser Ile Gln
    50                  55                  60

<210> SEQ ID NO 65
<211> LENGTH: 63
<212> TYPE: PRT
<213> ORGANISM: Artificial Sequence
<220> FEATURE:
<223> OTHER INFORMATION: IL-17A binder A7_2

<400> SEQUENCE: 65

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
                20                  25                  30

Ser Asp Gly Glu Trp Trp Phe Ala Arg Ser Leu Thr Thr Gly Glu Gly
            35                  40                  45

Gly Tyr Ile Pro Ser Asn Tyr Val Ala Pro Val Asp Ser Ile Gln
        50                  55                  60
```

<210> SEQ ID NO 66
<211> LENGTH: 63
<212> TYPE: PRT
<213> ORGANISM: Artificial Sequence
<220> FEATURE:
<223> OTHER INFORMATION: IL-17A binder C2_3

<400> SEQUENCE: 66

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
                20                  25                  30

Ser Asp Gly Glu Trp Trp Phe Ala Arg Ser Leu Thr Thr Gly Glu Asp
            35                  40                  45

Gly Tyr Ile Pro Ser Asn Tyr Val Ala Pro Val Asp Ser Ile Gln
        50                  55                  60
```

<210> SEQ ID NO 67
<211> LENGTH: 63
<212> TYPE: PRT
<213> ORGANISM: Artificial Sequence
<220> FEATURE:
<223> OTHER INFORMATION: IL-17A binder A3_3

<400> SEQUENCE: 67

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
                20                  25                  30

Ser Asp Gly Glu Trp Trp Val Ala Arg Ser Leu Thr Thr Gly Glu Ala
            35                  40                  45

Gly Tyr Ile Pro Ser Asn Tyr Val Ala Pro Val Asp Ser Ile Gln
        50                  55                  60
```

<210> SEQ ID NO 68
<211> LENGTH: 63
<212> TYPE: PRT
<213> ORGANISM: Artificial Sequence
<220> FEATURE:
<223> OTHER INFORMATION: IL-17A binder C1_2

<400> SEQUENCE: 68

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
                20                  25                  30

Ser Asp Gly Glu Trp Trp Leu Ala Arg Ser Leu Thr Thr Gly Glu Ala
            35                  40                  45

Gly Tyr Ile Pro Ser Asn Tyr Val Ala Pro Val Asp Ser Ile Gln
        50                  55                  60
```

```
<210> SEQ ID NO 69
<211> LENGTH: 63
<212> TYPE: PRT
<213> ORGANISM: Artificial Sequence
<220> FEATURE:
<223> OTHER INFORMATION: IL-17A binder E9

<400> SEQUENCE: 69

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Phe Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60

<210> SEQ ID NO 70
<211> LENGTH: 63
<212> TYPE: PRT
<213> ORGANISM: Artificial Sequence
<220> FEATURE:
<223> OTHER INFORMATION: IL-17A binder D1

<400> SEQUENCE: 70

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ser Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 71
<211> LENGTH: 63
<212> TYPE: PRT
<213> ORGANISM: Artificial Sequence
<220> FEATURE:
<223> OTHER INFORMATION: IL-17A binder B3_3

<400> SEQUENCE: 71

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 72
<211> LENGTH: 63
<212> TYPE: PRT
<213> ORGANISM: Artificial Sequence
<220> FEATURE:
<223> OTHER INFORMATION: IL-17A binder A12

<400> SEQUENCE: 72

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Thr Leu
```

```
            20                  25                  30

Ser Asp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 73
<211> LENGTH: 63
<212> TYPE: PRT
<213> ORGANISM: Artificial Sequence
<220> FEATURE:
<223> OTHER INFORMATION: IL-17A binder H3

<400> SEQUENCE: 73

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Leu Glu
            20                  25                  30

Ser Asp Gly Ser Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 74
<211> LENGTH: 63
<212> TYPE: PRT
<213> ORGANISM: Artificial Sequence
<220> FEATURE:
<223> OTHER INFORMATION: IL-17A binder H9

<400> SEQUENCE: 74

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Gln Val
            20                  25                  30

Ser Asp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 75
<211> LENGTH: 63
<212> TYPE: PRT
<213> ORGANISM: Artificial Sequence
<220> FEATURE:
<223> OTHER INFORMATION: IL-17A binder F1_2

<400> SEQUENCE: 75

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Lys
        35                  40                  45

Gly Tyr Ile Pro Ser Asn Tyr Val Ala Pro Val Asp Ser Ile Gln
    50                  55                  60

<210> SEQ ID NO 76
<211> LENGTH: 63
<212> TYPE: PRT
<213> ORGANISM: Artificial Sequence
```

-continued

```
<220> FEATURE:
<223> OTHER INFORMATION: IL-17A binder F10

<400> SEQUENCE: 76

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 77
<211> LENGTH: 63
<212> TYPE: PRT
<213> ORGANISM: Artificial Sequence
<220> FEATURE:
<223> OTHER INFORMATION: IL-17A binder C5_2

<400> SEQUENCE: 77

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60

<210> SEQ ID NO 78
<211> LENGTH: 63
<212> TYPE: PRT
<213> ORGANISM: Artificial Sequence
<220> FEATURE:
<223> OTHER INFORMATION: IL-17A binder D7_2

<400> SEQUENCE: 78

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60

<210> SEQ ID NO 79
<211> LENGTH: 63
<212> TYPE: PRT
<213> ORGANISM: Artificial Sequence
<220> FEATURE:
<223> OTHER INFORMATION: IL-17A binder C2_4

<400> SEQUENCE: 79

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Glu Ala Arg Ser Leu Thr Thr Gly Glu Ser
        35                  40                  45
```

```
Gly Tyr Ile Pro Ser Asn Tyr Val Ala Pro Val Asp Ser Ile Gln
        50                  55                  60
```

<210> SEQ ID NO 80
<211> LENGTH: 63
<212> TYPE: PRT
<213> ORGANISM: Artificial Sequence
<220> FEATURE:
<223> OTHER INFORMATION: IL-17A binder E3_1

<400> SEQUENCE: 80

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Ala Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 81
<211> LENGTH: 63
<212> TYPE: PRT
<213> ORGANISM: Artificial Sequence
<220> FEATURE:
<223> OTHER INFORMATION: IL-17A binder A11

<400> SEQUENCE: 81

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 82
<211> LENGTH: 63
<212> TYPE: PRT
<213> ORGANISM: Artificial Sequence
<220> FEATURE:
<223> OTHER INFORMATION: IL-17A binder B4_2

<400> SEQUENCE: 82

```
Gly Val Thr Leu Phe Val Ala Leu Tyr Asp Tyr Lys Ala Phe Trp Pro
1               5                   10                  15

Gly Asp Val Ser Phe His Lys Gly Glu Lys Phe Gln Ile Leu Arg Thr
            20                  25                  30

Ser Asp Gly Glu Trp Trp Leu Ala Arg Ser Leu Thr Thr Gly Glu Tyr
        35                  40                  45

Gly Tyr Ile Pro Ser Asn Tyr Val Ala Pro Val Asp Ser Ile Gln
    50                  55                  60
```

<210> SEQ ID NO 83
<211> LENGTH: 63
<212> TYPE: PRT
<213> ORGANISM: Artificial Sequence
<220> FEATURE:
<223> OTHER INFORMATION: IL-17A binder D10

<400> SEQUENCE: 83

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ser Ala Arg Ser Leu Thr Thr Gly Glu Val
        35                  40                  45

Gly Tyr Ile Pro Ser Asn Tyr Val Ala Pro Val Asp Ser Ile Gln
    50                  55                  60
```

<210> SEQ ID NO 84
<211> LENGTH: 63
<212> TYPE: PRT
<213> ORGANISM: Artificial Sequence
<220> FEATURE:
<223> OTHER INFORMATION: IL-17A binder E6_2

<400> SEQUENCE: 84

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Leu Trp Trp Phe Ala Arg Ser Leu Thr Thr Gly Glu Asp
        35                  40                  45

Gly Tyr Ile Pro Ser Asn Tyr Val Ala Pro Val Asp Ser Ile Gln
    50                  55                  60
```

<210> SEQ ID NO 85
<211> LENGTH: 63
<212> TYPE: PRT
<213> ORGANISM: Artificial Sequence
<220> FEATURE:
<223> OTHER INFORMATION: IL-17A binder H11_2

<400> SEQUENCE: 85

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Glu Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60
```

<210> SEQ ID NO 86
<211> LENGTH: 63
<212> TYPE: PRT
<213> ORGANISM: Artificial Sequence
<220> FEATURE:
<223> OTHER INFORMATION: IL-17A binder A5_3

<400> SEQUENCE: 86

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asn Trp Trp Glu Ala Arg Ser Leu Thr Thr Gly Glu Ala
        35                  40                  45

Gly Tyr Ile Pro Ser Asn Tyr Val Ala Pro Val Asp Ser Ile Gln
    50                  55                  60
```

<210> SEQ ID NO 87
<211> LENGTH: 63
<212> TYPE: PRT
<213> ORGANISM: Artificial Sequence
<220> FEATURE:
<223> OTHER INFORMATION: IL-17A binder F12

<400> SEQUENCE: 87

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Asp Ala Arg Ser Leu Thr Thr Gly Glu Arg
        35                  40                  45

Gly Tyr Ile Pro Ser Asn Tyr Val Ala Pro Val Asp Ser Ile Gln
    50                  55                  60
```

<210> SEQ ID NO 88
<211> LENGTH: 63
<212> TYPE: PRT
<213> ORGANISM: Artificial Sequence
<220> FEATURE:
<223> OTHER INFORMATION: IL-17A binder B7_2

<400> SEQUENCE: 88

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Val Ala Arg Ser Leu Thr Thr Gly Glu Asp
        35                  40                  45

Gly Tyr Ile Pro Ser Asn Tyr Val Ala Pro Val Asp Ser Ile Gln
    50                  55                  60
```

<210> SEQ ID NO 89
<211> LENGTH: 63
<212> TYPE: PRT
<213> ORGANISM: Artificial Sequence
<220> FEATURE:
<223> OTHER INFORMATION: IL-17A binder G2_2

<400> SEQUENCE: 89

```
Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Gly
            20                  25                  30

Ser Asp Gly Asp Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60
```

<210> SEQ ID NO 90
<211> LENGTH: 63
<212> TYPE: PRT
<213> ORGANISM: Artificial Sequence
<220> FEATURE:
<223> OTHER INFORMATION: IL-17A binder C5_3

<400> SEQUENCE: 90

```
Gly Val Thr Leu Phe Val Ala Leu Tyr Asp Tyr Lys Ala Phe Trp Pro
1               5                   10                  15
```

Gly Asp Leu Ser Phe His Lys Gly Glu Lys Phe Gln Ile Leu Arg Thr
            20                  25                  30

Ser Asp Gly Tyr Trp Trp Glu Ala Arg Ser Leu Thr Thr Gly Glu Asn
        35                  40                  45

Gly Tyr Ile Pro Ser Asn Tyr Val Ala Pro Val Asp Ser Ile Gln
    50                  55                  60

```
<210> SEQ ID NO 91
<211> LENGTH: 63
<212> TYPE: PRT
<213> ORGANISM: Artificial Sequence
<220> FEATURE:
<223> OTHER INFORMATION: IL-17A binder G11

<400> SEQUENCE: 91
```

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Asp Trp Trp Thr Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

```
<210> SEQ ID NO 92
<211> LENGTH: 63
<212> TYPE: PRT
<213> ORGANISM: Artificial Sequence
<220> FEATURE:
<223> OTHER INFORMATION: IL-17A binder F5

<400> SEQUENCE: 92
```

Gly Val Thr Leu Phe Val Ala Leu Tyr Asp Tyr Lys Ala Phe Trp Pro
1               5                   10                  15

Gly Asp Met Ser Phe His Lys Gly Glu Lys Phe Gln Ile Leu Arg Thr
            20                  25                  30

Ser Asp Gly Ile Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

```
<210> SEQ ID NO 93
<211> LENGTH: 63
<212> TYPE: PRT
<213> ORGANISM: Artificial Sequence
<220> FEATURE:
<223> OTHER INFORMATION: IL-17A binder D3_4

<400> SEQUENCE: 93
```

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Gln Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

```
<210> SEQ ID NO 94
<211> LENGTH: 63
<212> TYPE: PRT
```

<213> ORGANISM: Artificial Sequence
<220> FEATURE:
<223> OTHER INFORMATION: IL-17A binder F9

<400> SEQUENCE: 94

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Ala Trp Trp Met Ala Arg Ser Leu Thr Thr Gly Glu Asn
        35                  40                  45

Gly Tyr Ile Pro Ser Asn Tyr Val Ala Pro Val Asp Ser Ile Gln
    50                  55                  60

<210> SEQ ID NO 95
<211> LENGTH: 63
<212> TYPE: PRT
<213> ORGANISM: Artificial Sequence
<220> FEATURE:
<223> OTHER INFORMATION: IL-17A binder F1_3

<400> SEQUENCE: 95

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Tyr Ala Arg Ser Leu Thr Thr Gly Glu Lys
        35                  40                  45

Gly Tyr Ile Pro Ser Asn Tyr Val Ala Pro Val Asp Ser Ile Gln
    50                  55                  60

<210> SEQ ID NO 96
<211> LENGTH: 63
<212> TYPE: PRT
<213> ORGANISM: Artificial Sequence
<220> FEATURE:
<223> OTHER INFORMATION: IL-17A binder A4

<400> SEQUENCE: 96

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Glu Gly
            20                  25                  30

Ser Trp Gly Glu Trp Trp Glu Ala Arg Ser Leu Thr Thr Gly Glu Thr
        35                  40                  45

Gly Tyr Ile Pro Ser Asn Tyr Val Ala Pro Val Asp Ser Ile Gln
    50                  55                  60

<210> SEQ ID NO 97
<211> LENGTH: 63
<212> TYPE: PRT
<213> ORGANISM: Artificial Sequence
<220> FEATURE:
<223> OTHER INFORMATION: IL-17A binder G5

<400> SEQUENCE: 97

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Ala Ile Thr Arg Thr
            20                  25                  30

Ser Asp Gly Asp Trp Trp Glu Ala Val Ser Leu Thr Thr Gly Glu Thr

```
                  35                  40                  45

Gly Tyr Ile Pro Ser Asn Tyr Val Ala Pro Val Asp Ser Ile Gln
    50                  55                  60

<210> SEQ ID NO 98
<211> LENGTH: 63
<212> TYPE: PRT
<213> ORGANISM: Artificial Sequence
<220> FEATURE:
<223> OTHER INFORMATION: IL-17A binder A6_2

<400> SEQUENCE: 98

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Lys Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 99
<211> LENGTH: 63
<212> TYPE: PRT
<213> ORGANISM: Artificial Sequence
<220> FEATURE:
<223> OTHER INFORMATION: IL-17A binder D2_6

<400> SEQUENCE: 99

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Thr Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 100
<211> LENGTH: 63
<212> TYPE: PRT
<213> ORGANISM: Artificial Sequence
<220> FEATURE:
<223> OTHER INFORMATION: IL-17A binder G4_3

<400> SEQUENCE: 100

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Leu Ile Thr Arg Thr
            20                  25                  30

Ser Asp Gly Glu Trp Trp Val Ala Val Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 101
<211> LENGTH: 63
<212> TYPE: PRT
<213> ORGANISM: Artificial Sequence
<220> FEATURE:
<223> OTHER INFORMATION: IL-17A binder E3_2
```

```
<400> SEQUENCE: 101

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Glu Ile Val Arg Thr
            20                  25                  30

Ser Asp Gly Glu Trp Trp Val Ala Phe Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 102
<211> LENGTH: 63
<212> TYPE: PRT
<213> ORGANISM: Artificial Sequence
<220> FEATURE:
<223> OTHER INFORMATION: IL-17A binder B4_3

<400> SEQUENCE: 102

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Leu Ile Leu Arg Thr
            20                  25                  30

Ser Asp Gly Glu Trp Trp Val Ala Gln Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 103
<211> LENGTH: 63
<212> TYPE: PRT
<213> ORGANISM: Artificial Sequence
<220> FEATURE:
<223> OTHER INFORMATION: IL-17A binder C4_3

<400> SEQUENCE: 103

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe His Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 104
<211> LENGTH: 63
<212> TYPE: PRT
<213> ORGANISM: Artificial Sequence
<220> FEATURE:
<223> OTHER INFORMATION: IL-17A binder C9

<400> SEQUENCE: 104

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Phe Ile Leu Arg Thr
            20                  25                  30

Ser Asp Gly Glu Trp Trp Val Ala Gln Ser Leu Thr Thr Gly Glu Glu
        35                  40                  45

Gly Tyr Ile Pro Ser Asn Tyr Val Ala Pro Val Asp Ser Ile Gln
    50                  55                  60
```

```
<210> SEQ ID NO 105
<211> LENGTH: 63
<212> TYPE: PRT
<213> ORGANISM: Artificial Sequence
<220> FEATURE:
<223> OTHER INFORMATION: IL-17A binder E1_2

<400> SEQUENCE: 105

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ile Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 106
<211> LENGTH: 63
<212> TYPE: PRT
<213> ORGANISM: Artificial Sequence
<220> FEATURE:
<223> OTHER INFORMATION: IL-17A binder H2

<400> SEQUENCE: 106

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Arg Ile Lys Arg Thr
            20                  25                  30

Ser Asp Gly Glu Trp Trp Val Ala Val Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 107
<211> LENGTH: 63
<212> TYPE: PRT
<213> ORGANISM: Artificial Sequence
<220> FEATURE:
<223> OTHER INFORMATION: IL-17A binder 2C1

<400> SEQUENCE: 107

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 108
<211> LENGTH: 63
<212> TYPE: PRT
<213> ORGANISM: Artificial Sequence
<220> FEATURE:
<223> OTHER INFORMATION: IL-17A binder 1E2

<400> SEQUENCE: 108

Gly Val Thr Leu Phe Val Ala Leu Tyr Asp Tyr Arg Ala Phe Trp Pro
1               5                   10                  15
```

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 109
<211> LENGTH: 63
<212> TYPE: PRT
<213> ORGANISM: Artificial Sequence
<220> FEATURE:
<223> OTHER INFORMATION: IL-17A binder 1E9

<400> SEQUENCE: 109

Gly Val Thr Leu Phe Val Ala Leu Tyr Asp Tyr Lys Ala Ile Trp Pro
1               5                   10                  15

Thr Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 110
<211> LENGTH: 63
<212> TYPE: PRT
<213> ORGANISM: Artificial Sequence
<220> FEATURE:
<223> OTHER INFORMATION: IL-17A binder 1F3

<400> SEQUENCE: 110

Gly Val Thr Leu Phe Val Ala Leu Tyr Asp Tyr Lys Ala Phe Gly Pro
1               5                   10                  15

Gly Asp Ile Ser Phe His Lys Gly Glu Lys Phe Gln Ile Leu Arg Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 111
<211> LENGTH: 63
<212> TYPE: PRT
<213> ORGANISM: Artificial Sequence
<220> FEATURE:
<223> OTHER INFORMATION: IL-17A binder 2A6

<400> SEQUENCE: 111

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu His Thr
            20                  25                  30

Ser Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 112
<211> LENGTH: 63

```
<212> TYPE: PRT
<213> ORGANISM: Artificial Sequence
<220> FEATURE:
<223> OTHER INFORMATION: IL-17A binder 34D3

<400> SEQUENCE: 112

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Arg Asp Gly Glu Trp Trp Val Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 113
<211> LENGTH: 63
<212> TYPE: PRT
<213> ORGANISM: Artificial Sequence
<220> FEATURE:
<223> OTHER INFORMATION: IL-17A binder COMB3

<400> SEQUENCE: 113

Gly Val Thr Leu Phe Val Ala Leu Tyr Asp Tyr Lys Ala Phe Trp Pro
1               5                   10                  15

Gly Asp Leu Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln
    50                  55                  60

<210> SEQ ID NO 114
<211> LENGTH: 63
<212> TYPE: PRT
<213> ORGANISM: Artificial Sequence
<220> FEATURE:
<223> OTHER INFORMATION: IL-17A binder COMB4

<400> SEQUENCE: 114

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Ser
        35                  40                  45

Gly Tyr Ile Pro Ser Asn Tyr Val Ala Pro Val Asp Ser Ile Gln
    50                  55                  60

<210> SEQ ID NO 115
<211> LENGTH: 63
<212> TYPE: PRT
<213> ORGANISM: Artificial Sequence
<220> FEATURE:
<223> OTHER INFORMATION: IL-17A binder COMB5

<400> SEQUENCE: 115

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu His Thr
            20                  25                  30
```

Ser Asp Gly Glu Trp Trp Ile Ala Arg Ser Leu Thr Gly Glu Glu
            35                  40                  45

Gly Tyr Ile Pro Ser Asn Tyr Val Ala Pro Val Asp Ser Ile Gln
        50                  55                  60

<210> SEQ ID NO 116
<211> LENGTH: 63
<212> TYPE: PRT
<213> ORGANISM: Artificial Sequence
<220> FEATURE:
<223> OTHER INFORMATION: IL-17A binder COMB6

<400> SEQUENCE: 116

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
                20                  25                  30

Ser Asp Gly Glu Trp Trp Ile Ala Lys Ser Leu Thr Thr Gly Glu Glu
            35                  40                  45

Gly Tyr Ile Pro Ser Asn Tyr Val Ala Pro Val Asp Ser Ile Gln
        50                  55                  60

<210> SEQ ID NO 117
<211> LENGTH: 292
<212> TYPE: PRT
<213> ORGANISM: Artificial Sequence
<220> FEATURE:
<223> OTHER INFORMATION: Fusion protein E4-Fc

<400> SEQUENCE: 117

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
                20                  25                  30

Ser Asp Gly Glu Trp Trp Val Ala Arg Ser Leu Thr Thr Gly Glu Glu
            35                  40                  45

Gly Tyr Ile Pro Ser Asn Tyr Val Ala Pro Val Asp Ser Ile Gln Arg
        50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
            245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
        290

<210> SEQ ID NO 118
<211> LENGTH: 292
<212> TYPE: PRT
<213> ORGANISM: Artificial Sequence
<220> FEATURE:
<223> OTHER INFORMATION: Fusion protein 2C1-Fc

<400> SEQUENCE: 118

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Arg
    50                  55                  60

Ser Asp Lys Thr His Thr Cys Pro Pro Cys Pro Ala Pro Glu Leu Leu
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

```
Ser Pro Gly Lys
        290
```

<210> SEQ ID NO 119
<211> LENGTH: 365
<212> TYPE: PRT
<213> ORGANISM: Artificial Sequence
<220> FEATURE:
<223> OTHER INFORMATION: Fusion protein (2C1)_2-Fc

<400> SEQUENCE: 119

```
Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Ser Gly Val Thr Leu Phe Val Ala
65                  70                  75                  80

Leu Tyr Asp Tyr Lys Ala Phe Trp Pro Gly Asp Ile Ser Phe His Lys
                85                  90                  95

Gly Glu Lys Phe Gln Ile Leu Arg Thr Ser Asp Gly Glu Trp Trp Ile
            100                 105                 110

Ala Arg Ser Leu Thr Thr Gly Glu Glu Gly Tyr Ile Pro Ser Asn Tyr
        115                 120                 125

Val Ala Pro Val Asp Ser Ile Gln Arg Ser Asp Lys Thr His Thr Cys
    130                 135                 140

Pro Pro Cys Pro Ala Pro Glu Leu Leu Gly Gly Pro Ser Val Phe Leu
145                 150                 155                 160

Phe Pro Pro Lys Pro Lys Asp Thr Leu Met Ile Ser Arg Thr Pro Glu
                165                 170                 175

Val Thr Cys Val Val Val Asp Val Ser His Glu Asp Pro Glu Val Lys
            180                 185                 190

Phe Asn Trp Tyr Val Asp Gly Val Glu Val His Asn Ala Lys Thr Lys
        195                 200                 205

Pro Arg Glu Glu Gln Tyr Asn Ser Thr Tyr Arg Val Val Ser Val Leu
    210                 215                 220

Thr Val Leu His Gln Asp Trp Leu Asn Gly Lys Glu Tyr Lys Cys Lys
225                 230                 235                 240

Val Ser Asn Lys Ala Leu Pro Ala Pro Ile Glu Lys Thr Ile Ser Lys
                245                 250                 255

Ala Lys Gly Gln Pro Arg Glu Pro Gln Val Tyr Thr Leu Pro Pro Ser
            260                 265                 270

Arg Glu Glu Met Thr Lys Asn Gln Val Ser Leu Thr Cys Leu Val Lys
        275                 280                 285

Gly Phe Tyr Pro Ser Asp Ile Ala Val Glu Trp Glu Ser Asn Gly Gln
    290                 295                 300

Pro Glu Asn Asn Tyr Lys Thr Thr Pro Val Leu Asp Ser Asp Gly
305                 310                 315                 320

Ser Phe Phe Leu Tyr Ser Lys Leu Thr Val Asp Lys Ser Arg Trp Gln
                325                 330                 335

Gln Gly Asn Val Phe Ser Cys Ser Val Met His Glu Ala Leu His Asn
            340                 345                 350
```

His Tyr Thr Gln Lys Ser Leu Ser Leu Ser Pro Gly Lys
         355                 360                 365

<210> SEQ ID NO 120
<211> LENGTH: 10
<212> TYPE: PRT
<213> ORGANISM: Artificial Sequence
<220> FEATURE:
<223> OTHER INFORMATION: Amino acid linker

<400> SEQUENCE: 120

Gly Gly Gly Gly Ser Gly Gly Gly Gly Ser
1               5                   10

<210> SEQ ID NO 121
<211> LENGTH: 29
<212> TYPE: DNA
<213> ORGANISM: Artificial Sequence
<220> FEATURE:
<223> OTHER INFORMATION: PCR primer fm5

<400> SEQUENCE: 121
atcgggatcc gacaaaactc acacatgcc                                         29

<210> SEQ ID NO 122
<211> LENGTH: 30
<212> TYPE: DNA
<213> ORGANISM: Artificial Sequence
<220> FEATURE:
<223> OTHER INFORMATION: PCR primer fm6

<400> SEQUENCE: 122
tacgaagctt tcatttaccc ggagacaggg                                        30

<210> SEQ ID NO 123
<211> LENGTH: 44
<212> TYPE: DNA
<213> ORGANISM: Artificial Sequence
<220> FEATURE:
<223> OTHER INFORMATION: PCR primer fm7

<400> SEQUENCE: 123
atatcaccat ggggccggag tgacactctt tgtggcccttt tatg                       44

<210> SEQ ID NO 124
<211> LENGTH: 31
<212> TYPE: DNA
<213> ORGANISM: Artificial Sequence
<220> FEATURE:
<223> OTHER INFORMATION: PCR primer fm8

<400> SEQUENCE: 124
cgtaggatcc ctggatagag tcaactggag c                                      31

<210> SEQ ID NO 125
<211> LENGTH: 54
<212> TYPE: DNA
<213> ORGANISM: Artificial Sequence
<220> FEATURE:
<223> OTHER INFORMATION: PCR primer 47b.fo

<400> SEQUENCE: 125
agagccacct ccgcctgaac cgcctccacc ctggatagag tcaactggag ccac             54

<210> SEQ ID NO 126

```
<211> LENGTH: 48
<212> TYPE: DNA
<213> ORGANISM: Artificial Sequence
<220> FEATURE:
<223> OTHER INFORMATION: PCR primer 52. ba

<400> SEQUENCE: 126
gactaacgag atcgcggatc cggagtgaca ctctttgtgg ccctttat              48

<210> SEQ ID NO 127
<211> LENGTH: 57
<212> TYPE: DNA
<213> ORGANISM: Artificial Sequence
<220> FEATURE:
<223> OTHER INFORMATION: PCR primer 48b.ba

<400> SEQUENCE: 127
ggtggaggcg gttcaggcgg aggtggctct ggagtgacac tctttgtggc cctttat    57

<210> SEQ ID NO 128
<211> LENGTH: 87
<212> TYPE: DNA
<213> ORGANISM: Artificial Sequence
<220> FEATURE:
<223> OTHER INFORMATION: PCR primer 51. fo

<400> SEQUENCE: 128
atcccaagct tagtgatggt gatggtgatg cagatcctct tctgagatga gttttgttc  60 accctggata gagtcaactg gagccac                                     87

<210> SEQ ID NO 129
<211> LENGTH: 145
<212> TYPE: PRT
<213> ORGANISM: Macaca fascicularis

<400> SEQUENCE: 129

Gly Ser Ile Val Lys Ala Gly Ile Ala Ile Pro Arg Asn Ser Gly Cys
1               5                  10                  15

Pro Asn Ser Glu Asp Lys Asn Phe Pro Arg Thr Val Met Val Asn Leu
            20                  25                  30

Asn Ile His Asn Arg Asn Thr Ser Thr Asn Pro Lys Arg Ser Ser Asp
        35                  40                  45

Tyr Tyr Asn Arg Ser Thr Ser Pro Trp Asn Leu His Arg Asn Glu Asp
    50                  55                  60

Pro Glu Arg Tyr Pro Ser Val Ile Trp Glu Ala Lys Cys Arg His Leu
65                  70                  75                  80

Gly Cys Val Lys Ala Asp Gly Asn Val Asp Tyr His Met Asn Ser Val
                85                  90                  95

Pro Ile Gln Gln Glu Ile Leu Val Leu Arg Arg Glu Pro Arg His Cys
            100                 105                 110

Pro Asn Ser Phe Arg Leu Glu Lys Ile Leu Val Ser Val Gly Cys Thr
        115                 120                 125

Cys Val Thr Pro Ile Val His Val Ala Gly His His His His
    130                 135                 140

His
145

<210> SEQ ID NO 130
<211> LENGTH: 292
<212> TYPE: PRT
<213> ORGANISM: Homo sapiens
```

<400> SEQUENCE: 130

```
Gly Val Thr Leu Phe Val Ala Leu Tyr Asp Tyr Lys Ala Phe Trp Pro
1               5                   10                  15
Gly Asp Ile Ser Phe His Lys Gly Glu Lys Phe Gln Ile Leu Arg Thr
            20                  25                  30
Ser Asp Gly Glu Trp Trp Ile Ala Arg Ser Leu Thr Thr Gly Glu Glu
        35                  40                  45
Gly Tyr Ile Pro Ser Asn Tyr Val Ala Pro Val Asp Ser Ile Gln Arg
    50                  55                  60
Ser Asp Lys Thr His Thr Cys Pro Pro Cys Pro Ala Pro Glu Leu Leu
65                  70                  75                  80
Gly Gly Pro Ser Val Phe Leu Phe Pro Pro Lys Pro Lys Asp Thr Leu
                85                  90                  95
Met Ile Ser Arg Thr Pro Glu Val Thr Cys Val Val Val Asp Val Ser
            100                 105                 110
His Glu Asp Pro Glu Val Lys Phe Asn Trp Tyr Val Asp Gly Val Glu
        115                 120                 125
Val His Asn Ala Lys Thr Lys Pro Arg Glu Glu Gln Tyr Asn Ser Thr
    130                 135                 140
Tyr Arg Val Val Ser Val Leu Thr Val Leu His Gln Asp Trp Leu Asn
145                 150                 155                 160
Gly Lys Glu Tyr Lys Cys Lys Val Ser Asn Lys Ala Leu Pro Ala Pro
                165                 170                 175
Ile Glu Lys Thr Ile Ser Lys Ala Lys Gly Gln Pro Arg Glu Pro Gln
            180                 185                 190
Val Tyr Thr Leu Pro Pro Ser Arg Glu Glu Met Thr Lys Asn Gln Val
        195                 200                 205
Ser Leu Thr Cys Leu Val Lys Gly Phe Tyr Pro Ser Asp Ile Ala Val
    210                 215                 220
Glu Trp Glu Ser Asn Gly Gln Pro Glu Asn Asn Tyr Lys Thr Thr Pro
225                 230                 235                 240
Pro Val Leu Asp Ser Asp Gly Ser Phe Phe Leu Tyr Ser Lys Leu Thr
                245                 250                 255
Val Asp Lys Ser Arg Trp Gln Gln Gly Asn Val Phe Ser Cys Ser Val
            260                 265                 270
Met His Glu Ala Leu His Asn His Tyr Thr Gln Lys Ser Leu Ser Leu
        275                 280                 285
Ser Pro Gly Lys
    290
```

<210> SEQ ID NO 131
<211> LENGTH: 292
<212> TYPE: PRT
<213> ORGANISM: Artificial sequence
<220> FEATURE:
<223> OTHER INFORMATION: 2C1-Fc(LALA)

<400> SEQUENCE: 131

```
Gly Val Thr Leu Phe Val Ala Leu Tyr Asp Tyr Lys Ala Phe Trp Pro
1               5                   10                  15
Gly Asp Ile Ser Phe His Lys Gly Glu Lys Phe Gln Ile Leu Arg Thr
            20                  25                  30
Ser Asp Gly Glu Trp Trp Ile Ala Arg Ser Leu Thr Thr Gly Glu Glu
        35                  40                  45
```

Gly Tyr Ile Pro Ser Asn Tyr Val Ala Pro Val Asp Ser Ile Gln Arg
            50                  55                  60

Ser Asp Lys Thr His Thr Cys Pro Pro Cys Pro Ala Pro Glu Ala Ala
 65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

His Glu Asp Pro Glu Val Lys Phe Asn Trp Tyr Val Asp Gly Val Glu
        115                 120                 125

Val His Asn Ala Lys Thr Lys Pro Arg Glu Glu Gln Tyr Asn Ser Thr
130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Ala Leu Pro Ala Pro
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Arg Glu Glu Met Thr Lys Asn Gln Val
        195                 200                 205

Ser Leu Thr Cys Leu Val Lys Gly Phe Tyr Pro Ser Asp Ile Ala Val
210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Lys Leu Thr
                245                 250                 255

Val Asp Lys Ser Arg Trp Gln Gln Gly Asn Val Phe Ser Cys Ser Val
            260                 265                 270

Met His Glu Ala Leu His Asn His Tyr Thr Gln Lys Ser Leu Ser Leu
        275                 280                 285

Ser Pro Gly Lys
    290

<210> SEQ ID NO 132
<211> LENGTH: 295
<212> TYPE: PRT
<213> ORGANISM: Artificial sequence
<220> FEATURE:
<223> OTHER INFORMATION: 2C1-m5E-Fc(LALA)

<400> SEQUENCE: 132

Gly Val Thr Leu Phe Val Ala Leu Tyr Asp Tyr Lys Ala Phe Trp Pro
 1               5                  10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Glu
    50                  55                  60

Pro Lys Ser Ser Asp Lys Thr His Thr Cys Pro Pro Cys Pro Ala Pro
 65                  70                  75                  80

Glu Ala Ala Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

```
Asp Val Ser His Glu Asp Pro Glu Val Lys Phe Asn Trp Tyr Val Asp
            115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Glu Glu Met Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295

<210> SEQ ID NO 133
<211> LENGTH: 295
<212> TYPE: PRT
<213> ORGANISM: Artificial sequence
<220> FEATURE:
<223> OTHER INFORMATION: 2C1-m5-Fc(LALA)

<400> SEQUENCE: 133

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Asp Lys Thr His Thr Cys Pro Pro Cys Pro Ala Pro
65                  70                  75                  80

Glu Ala Ala Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175
```

```
Pro Ala Pro Ile Glu Lys Thr Ile Ser Lys Ala Lys Gly Gln Pro Arg
                180                 185                 190

Glu Pro Gln Val Tyr Thr Leu Pro Pro Ser Arg Glu Glu Met Thr Lys
            195                 200                 205

Asn Gln Val Ser Leu Thr Cys Leu Val Lys Gly Phe Tyr Pro Ser Asp
        210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
        290                 295

<210> SEQ ID NO 134
<211> LENGTH: 300
<212> TYPE: PRT
<213> ORGANISM: Artificial sequence
<220> FEATURE:
<223> OTHER INFORMATION: 2C1-m10-Fc(LALA)

<400> SEQUENCE: 134

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Ser Asp Lys Thr His Thr Cys Pro
65                  70                  75                  80

Pro Cys Pro Ala Pro Glu Ala Ala Gly Gly Pro Ser Val Phe Leu Phe
                85                  90                  95

Pro Pro Lys Pro Lys Asp Thr Leu Met Ile Ser Arg Thr Pro Glu Val
            100                 105                 110

Thr Cys Val Val Val Asp Val Ser His Glu Asp Pro Glu Val Lys Phe
        115                 120                 125

Asn Trp Tyr Val Asp Gly Val Glu Val His Asn Ala Lys Thr Lys Pro
    130                 135                 140

Arg Glu Glu Gln Tyr Asn Ser Thr Tyr Arg Val Val Ser Val Leu Thr
145                 150                 155                 160

Val Leu His Gln Asp Trp Leu Asn Gly Lys Glu Tyr Lys Cys Lys Val
                165                 170                 175

Ser Asn Lys Ala Leu Pro Ala Pro Ile Glu Lys Thr Ile Ser Lys Ala
            180                 185                 190

Lys Gly Gln Pro Arg Glu Pro Gln Val Tyr Thr Leu Pro Pro Ser Arg
        195                 200                 205

Glu Glu Met Thr Lys Asn Gln Val Ser Leu Thr Cys Leu Val Lys Gly
    210                 215                 220

Phe Tyr Pro Ser Asp Ile Ala Val Glu Trp Glu Ser Asn Gly Gln Pro
225                 230                 235                 240
```

Glu Asn Asn Tyr Lys Thr Thr Pro Val Leu Asp Ser Asp Gly Ser
            245                 250                 255

Phe Phe Leu Tyr Ser Lys Leu Thr Val Asp Lys Ser Arg Trp Gln Gln
        260                 265                 270

Gly Asn Val Phe Ser Cys Ser Val Met His Glu Ala Leu His Asn His
            275                 280                 285

Tyr Thr Gln Lys Ser Leu Ser Leu Ser Pro Gly Lys
        290                 295                 300

<210> SEQ ID NO 135
<211> LENGTH: 305
<212> TYPE: PRT
<213> ORGANISM: Artificial sequence
<220> FEATURE:
<223> OTHER INFORMATION: 2C1-m15-Fc(LALA)

<400> SEQUENCE: 135

Gly Val Thr Leu Phe Val Ala Leu Tyr Asp Tyr Lys Ala Phe Trp Pro
1               5                   10                  15

Gly Asp Ile Ser Phe His Lys Gly Glu Lys Phe Gln Ile Leu Arg Thr
            20                  25                  30

Ser Asp Gly Glu Trp Trp Ile Ala Arg Ser Leu Thr Thr Gly Glu Glu
        35                  40                  45

Gly Tyr Ile Pro Ser Asn Tyr Val Ala Pro Val Asp Ser Ile Gln Gly
    50                  55                  60

Gly Gly Gly Ser Gly Gly Gly Gly Ser Gly Gly Gly Gly Ser Asp Lys
65                  70                  75                  80

Thr His Thr Cys Pro Pro Cys Pro Ala Pro Glu Ala Ala Gly Gly Pro
                85                  90                  95

Ser Val Phe Leu Phe Pro Pro Lys Pro Lys Asp Thr Leu Met Ile Ser
            100                 105                 110

Arg Thr Pro Glu Val Thr Cys Val Val Val Asp Val Ser His Glu Asp
        115                 120                 125

Pro Glu Val Lys Phe Asn Trp Tyr Val Asp Gly Val Glu Val His Asn
    130                 135                 140

Ala Lys Thr Lys Pro Arg Glu Glu Gln Tyr Asn Ser Thr Tyr Arg Val
145                 150                 155                 160

Val Ser Val Leu Thr Val Leu His Gln Asp Trp Leu Asn Gly Lys Glu
                165                 170                 175

Tyr Lys Cys Lys Val Ser Asn Lys Ala Leu Pro Ala Pro Ile Glu Lys
            180                 185                 190

Thr Ile Ser Lys Ala Lys Gly Gln Pro Arg Glu Pro Gln Val Tyr Thr
        195                 200                 205

Leu Pro Pro Ser Arg Glu Glu Met Thr Lys Asn Gln Val Ser Leu Thr
    210                 215                 220

Cys Leu Val Lys Gly Phe Tyr Pro Ser Asp Ile Ala Val Glu Trp Glu
225                 230                 235                 240

Ser Asn Gly Gln Pro Glu Asn Asn Tyr Lys Thr Thr Pro Pro Val Leu
                245                 250                 255

Asp Ser Asp Gly Ser Phe Phe Leu Tyr Ser Lys Leu Thr Val Asp Lys
            260                 265                 270

Ser Arg Trp Gln Gln Gly Asn Val Phe Ser Cys Ser Val Met His Glu
        275                 280                 285

Ala Leu His Asn His Tyr Thr Gln Lys Ser Leu Ser Leu Ser Pro Gly
    290                 295                 300

Lys
305

<210> SEQ ID NO 136
<211> LENGTH: 30
<212> TYPE: DNA
<213> ORGANISM: Artificial sequence
<220> FEATURE:
<223> OTHER INFORMATION: Primer SB3

<400> SEQUENCE: 136
cgaattcggg agtgacactc tttgtggccc                                    30

<210> SEQ ID NO 137
<211> LENGTH: 30
<212> TYPE: DNA
<213> ORGANISM: Artificial sequence
<220> FEATURE:
<223> OTHER INFORMATION: Primer SB4

<400> SEQUENCE: 137
gaagatctct ggatagagtc aactggagcc                                    30

<210> SEQ ID NO 138
<211> LENGTH: 38
<212> TYPE: DNA
<213> ORGANISM: Artificial sequence
<220> FEATURE:
<223> OTHER INFORMATION: Primer SB5

<400> SEQUENCE: 138
cccaagcttg ggatgggcta caggatgcaa ctcctgtc                           38

<210> SEQ ID NO 139
<211> LENGTH: 30
<212> TYPE: DNA
<213> ORGANISM: Artificial sequence
<220> FEATURE:
<223> OTHER INFORMATION: Primer SB6

<400> SEQUENCE: 139
cgggatcctc atttacccgg agacagggag                                    30

<210> SEQ ID NO 140
<211> LENGTH: 36
<212> TYPE: DNA
<213> ORGANISM: Artificial sequence
<220> FEATURE:
<223> OTHER INFORMATION: Primer SB7

<400> SEQUENCE: 140
actgacggtc cccccgcggc ttcaggtgct gggcac                             36

<210> SEQ ID NO 141
<211> LENGTH: 32
<212> TYPE: DNA
<213> ORGANISM: Artificial sequence
<220> FEATURE:
<223> OTHER INFORMATION: Primer SB8

<400> SEQUENCE: 141
gccgcggggg gaccgtcagt cttcctcttc cc                                 32

<210> SEQ ID NO 142
<211> LENGTH: 39
<212> TYPE: DNA

```
<213> ORGANISM: Artificial sequence
<220> FEATURE:
<223> OTHER INFORMATION: Primer Ba_2C1_R_EPKSS

<400> SEQUENCE: 142
gctgcttttc ggttcctgga tagagtcaac tggagccac                    39

<210> SEQ ID NO 143
<211> LENGTH: 39
<212> TYPE: DNA
<213> ORGANISM: Artificial sequence
<220> FEATURE:
<223> OTHER INFORMATION: Primer Ba_Hinge_F_EPKSS

<400> SEQUENCE: 143
gaaccgaaaa gcagcgacaa aactcacaca tgcccaccg                    39

<210> SEQ ID NO 144
<211> LENGTH: 39
<212> TYPE: DNA
<213> ORGANISM: Artificial sequence
<220> FEATURE:
<223> OTHER INFORMATION: Primer 47c.fo

<400> SEQUENCE: 144
tgaaccgcct ccaccctgga tagagtcaac tggagccac                    39

<210> SEQ ID NO 145
<211> LENGTH: 39
<212> TYPE: DNA
<213> ORGANISM: Artificial sequence
<220> FEATURE:
<223> OTHER INFORMATION: Primer Ba_Hinge_F_5aaGS-linker

<400> SEQUENCE: 145
ggtggaggcg gttcagacaa aactcacaca tgcccaccg                    39

<210> SEQ ID NO 146
<211> LENGTH: 54
<212> TYPE: DNA
<213> ORGANISM: Artificial sequence
<220> FEATURE:
<223> OTHER INFORMATION: Primer 47b.fo

<400> SEQUENCE: 146
agagccacct ccgcctgaac cgcctccacc ctggatagag tcaactggag ccac   54

<210> SEQ ID NO 147
<211> LENGTH: 54
<212> TYPE: DNA
<213> ORGANISM: Artificial sequence
<220> FEATURE:
<223> OTHER INFORMATION: Primer Ba_Hinge_F_10aaGS-linker

<400> SEQUENCE: 147
ggtggaggcg gttcaggcgg aggtggctct gacaaaactc acacatgccc accg   54

<210> SEQ ID NO 148
<211> LENGTH: 69
<212> TYPE: DNA
<213> ORGANISM: Artificial sequence
<220> FEATURE:
<223> OTHER INFORMATION: Primer 47.fo.corr

<400> SEQUENCE: 148
tgatccgcca ccgccagagc cacctccgcc tgaaccgcct ccaccctgga tagagtcaac   60
```

```
tggagccac                                                              69

<210> SEQ ID NO 149
<211> LENGTH: 69
<212> TYPE: DNA
<213> ORGANISM: Artificial sequence
<220> FEATURE:
<223> OTHER INFORMATION: Primer Ba_Hinge_F_15aaGS-linker

<400> SEQUENCE: 149
ggtggaggcg gttcaggcgg aggtggctct ggcggtggcg gatcagacaa aactcacaca     60
tgcccaccg                                                              69
```